(12) United States Patent
Mansour et al.

(10) Patent No.: US 11,298,110 B2
(45) Date of Patent: Apr. 12, 2022

(54) DOPPLER MEASUREMENT SYSTEM AND METHOD

(71) Applicants: Omar Mansour, Randolph, NJ (US); James Lacefield, London (CA)

(72) Inventors: Omar Mansour, Randolph, NJ (US); James Lacefield, London (CA)

(73) Assignees: Omar Mansour, Randolph, NJ (US); James Lacefield, London (CA)

( * ) Notice: Subject to any disclaimer, the term of this patent is extended or adjusted under 35 U.S.C. 154(b) by 629 days.

(21) Appl. No.: 16/079,926

(22) PCT Filed: Feb. 24, 2017

(86) PCT No.: PCT/CA2017/050247
§ 371 (c)(1),
(2) Date: Aug. 24, 2018

(87) PCT Pub. No.: WO2017/143456
PCT Pub. Date: Aug. 31, 2017

(65) Prior Publication Data
US 2019/0046161 A1 Feb. 14, 2019

Related U.S. Application Data

(60) Provisional application No. 62/300,600, filed on Feb. 26, 2016.

(51) Int. Cl.
*A61B 8/08* (2006.01)
*A61B 8/06* (2006.01)
(Continued)

(52) U.S. Cl.
CPC ............... *A61B 8/488* (2013.01); *A61B 8/06* (2013.01); *A61B 8/4488* (2013.01);
(Continued)

(58) Field of Classification Search
CPC ......... A61B 8/488; A61B 8/06; A61B 8/4488; A61B 8/4494; A61B 8/463; A61B 8/5246;
(Continued)

(56) References Cited

U.S. PATENT DOCUMENTS 3,940,731 A    2/1976  Cooper et al.
4,542,657 A *  9/1985  Barber .................... A61B 8/06
                                                     324/76.15
(Continued)

OTHER PUBLICATIONS

Ekroll, et al. 2014 "On the accuracy of coherent compounding Doppler imaging" *IEEE International Ultrasonics Symposium Proceedings*; 1730-1733.
(Continued)

*Primary Examiner* — Rochelle D Turchen
*Assistant Examiner* — Chao Sheng
(74) *Attorney, Agent, or Firm* — Knobbe, Martens, Olson & Bear, LLP

(57) ABSTRACT

A Doppler measurement system includes a random generator outputting a control signal encoding a random selection, and an ultrasonic array transducer for emitting a sequence of transmit pulses at a target at either an adjustable steering angle (plane wave imaging) or from a selectable non-sequential transducer element order (synthetic aperture imaging) corresponding to the random selection and for receiving an echo of each transmit pulse reflected from the target. Each transmit pulse is independently adjusted to a steering angle (plane wave imaging) or selectable transducer element order (synthetic aperture imaging) corresponding to a unique random selection so that the sequence of transmit pulses is a random sweep. The system can also include a memory for storing echo data, and a processor connected to the memory for using transmit data and echo data to extract
(Continued)

a Doppler parameter. Methods of Doppler measurement and computer-readable medium can incorporating the measurement system.

20 Claims, 18 Drawing Sheets

(51) Int. Cl.
| | |
|---|---|
| G01S 15/50 | (2006.01) |
| G01F 1/66 | (2006.01) |
| G01S 15/89 | (2006.01) |
| A61B 8/00 | (2006.01) |
| G01S 7/52 | (2006.01) |
| G01F 1/663 | (2022.01) |

(52) U.S. Cl.
CPC ............ *A61B 8/4494* (2013.01); *A61B 8/463* (2013.01); *G01F 1/66* (2013.01); *G01F 1/663* (2013.01); *G01S 7/52095* (2013.01); *G01S 15/50* (2013.01); *G01S 15/8927* (2013.01); *G01S 15/8977* (2013.01); *G01S 15/8979* (2013.01); *G01S 15/8981* (2013.01); *G01S 15/8984* (2013.01); *G01S 15/8988* (2013.01); *A61B 8/5246* (2013.01)

(58) Field of Classification Search
CPC ........ G01F 1/66; G01F 1/663; G01S 7/52095; G01S 15/50; G01S 15/8927; G01S 15/8977; G01S 15/8979; G01S 15/8981; G01S 15/8984; G01S 15/8988
See application file for complete search history.

(56) References Cited

U.S. PATENT DOCUMENTS

| | | | |
|---|---|---|---|
| 5,048,528 | A | 9/1991 | Superina et al. |
| 6,193,663 | B1 | 2/2001 | Napolitano et al. |
| 6,436,046 | B1 | 8/2002 | Napolitano et al. |
| 6,552,964 | B2 * | 4/2003 | Chiang ............... G01S 7/52085 367/138 |
| 6,679,846 | B2 | 1/2004 | Napolitano et al. |
| 7,540,842 | B2 | 6/2009 | Napolitano et al. |
| 9,117,439 | B2 | 8/2015 | Bercoff et al. |
| 2009/0326379 | A1 | 12/2009 | Daigle et al. |
| 2013/0261463 | A1 * | 10/2013 | Chiang .................. A61B 8/488 600/447 |
| 2014/0371594 | A1 | 12/2014 | Flynn et al. |
| 2014/0378834 | A1 | 12/2014 | Napolitano et al. |
| 2015/0141832 | A1 | 5/2015 | Yu et al. |

OTHER PUBLICATIONS

Kasai, et al. 1985 "Real-time two-dimensional blood flow imaging using an autocorrelation technique" *IEEE Transactions on Sonics and Ultrasonics* SU-32(3): 458-464.

Kay & Marple 1981 "Spectrum analysis—A modern perspective" *Proceedings of the IEEE* 69(11): 1380-1419.

Montaldo, et al. 2009 "Coherent plane-wave compounding for very high frame rate ultrasonography and transient elastography" *IEEE Transactions on ultrasonics, Ferroelectrics, and frequency control* 56(3): 489-506.

Poepping, et al. 2004 "A thin-walled carotid vessel phantom for Doppler ultrasound flow studies" *Ultrasound in Med. & Biol.* 30(8): 1067-1078.

Ramnarine, et al. 1998 "Validation of a new blood-mimicking fluid for use in Doppler flow test objects" *Ultrasound in Med. & Biol.* 24(3): 451-459.

Shen, et al. 2010 "High frame-rate vector flow estimation using speckle tracking with recursive plane-wave compounding" *IEEE International Ultrasonics Symposium Proceedings*: 1307-1310.

Soumekh 1996 "Phased array imaging of moving targets with randomized beam steering and area spotlighting" *IEEE Inter Conf Image Process*: 919-922.

Vaitkus & Cobbold 1988 "A comparative study and assessment of Doppler ultrasound spectral estimation techniques part I: Estimation methods" *Ultrasound in Medicine & Biology* 14(8): 661-672.

Vaitkus & Cobbold 1988 "A comparative study and assessment of Doppler ultrasound spectral estimation techniques part II: Estimation methods" *Ultrasound in Medicine & Biology* 14(8): 673-688.

* cited by examiner

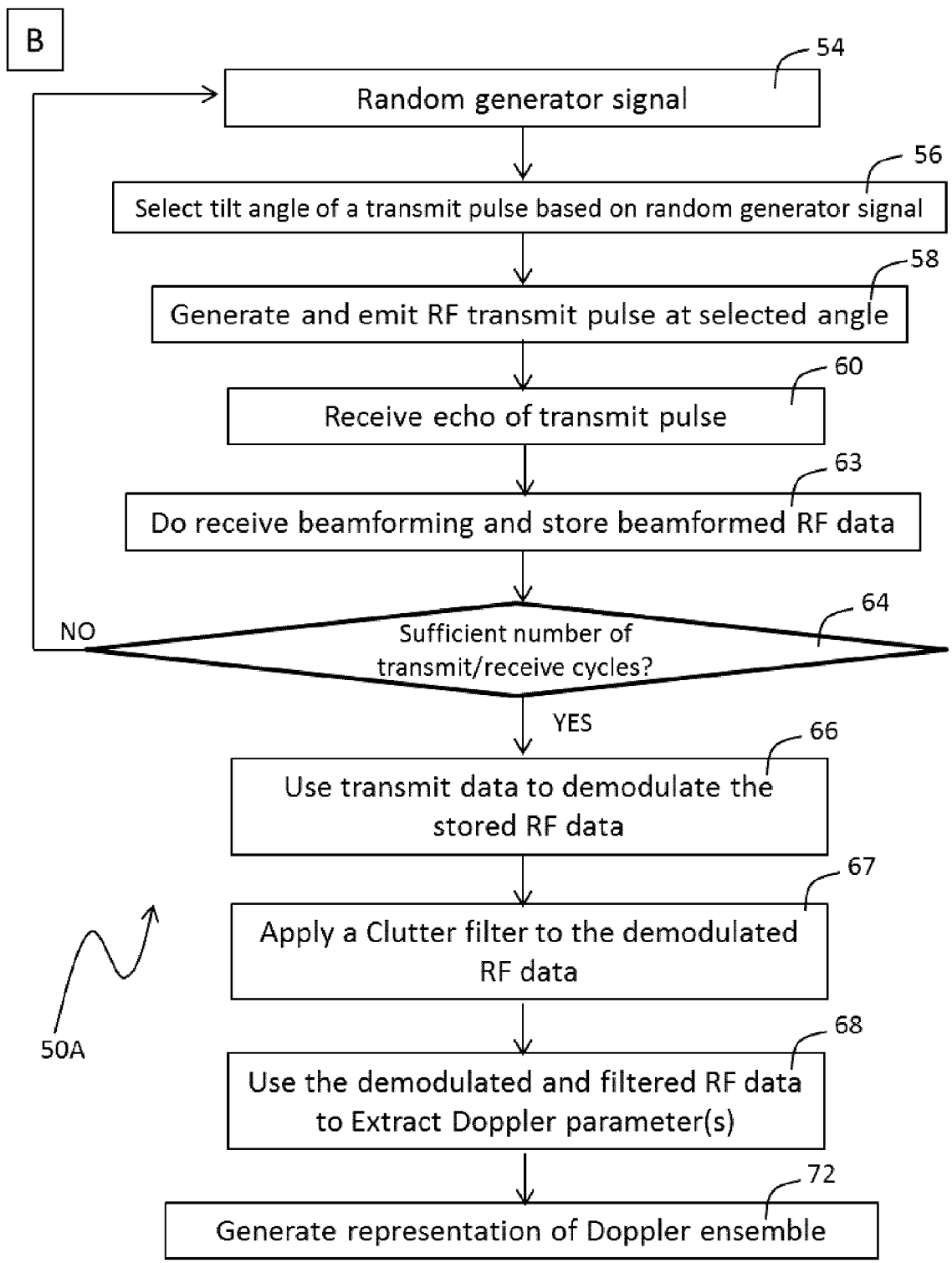

ial Application No. PCT/CA2017/050247, filed Feb. 24, 2017, designating the U.S. and published in English as WO 2017/143456 A1 on Aug. 31, 2017 which claims the benefit of U.S. Provisional Patent Application No. 62/300,600 filed Feb. 26, 2016. Any and all applications for which a foreign or domestic priority claim is identified here or in the Application Data Sheet as filed with the present application are hereby incorporated by reference under 37 CFR 1.57.

DOPPLER MEASUREMENT SYSTEM AND METHOD

CROSS REFERENCE TO RELATED APPLICATIONS

This application is the U.S. National Phase of International Application No. PCT/CA2017/050247, filed Feb. 24, 2017, designating the U.S. and published in English as WO 2017/143456 A1 on Aug. 31, 2017 which claims the benefit of U.S. Provisional Patent Application No. 62/300,600 filed Feb. 26, 2016. Any and all applications for which a foreign or domestic priority claim is identified here or in the Application Data Sheet as filed with the present application are hereby incorporated by reference under 37 CFR 1.57.

BACKGROUND OF THE INVENTION

Field of the Invention

The present invention relates to ultrasound measurement technology, and more particularly to ultrasonic Doppler measurement systems.

Description of the Related Art

Pulsed Doppler ultrasound systems can be used to measure motion, such as a flow of a liquid. For example, medical applications include measuring blood flow or tissue motion where ultrasonic pulses are directed into a human subject along a path which intersects a blood vessel or its surrounding tissue or a cardiac chamber or its surrounding tissue. For blood flow measurement, ultrasound energy from a transmitted pulse is backscattered from blood within the vessel or chamber and returns to a transducer where it is received and converted into an electrical signal. A Doppler shift occurs when the frequency of the scattered echoes is shifted, in relation to the frequency of the transmitted pulse, as occurs for example if the blood has a velocity component along the direction of propagation of the ultrasound pulse. The Doppler shift can be analyzed to yield diagnostic results, such as a numeric estimate of the blood velocity and/or a map of blood velocity as a function of position within the body.

In a more specific example of Doppler shift analysis, plane-wave imaging achieves high frame rates, enabling the capture of fast dynamic events required in various ultrasound applications. In conventional plane-wave imaging with coherent compounding, plane wave pulses are transmitted using a linear sequence of tilt angles of length N, producing low-resolution image (LRI) frames at a frame rate equal to a pulse repetition frequency (PRF). Summation is then performed along the N LRI frames to produce a single compounded high-resolution image (HRI), thereby implementing dynamic transmit focusing and achieving beam profiles similar to those in conventional narrow-beam transmit modes.

Frame compounding enables retrospective transmit and receive beamforming that significantly improves resolution for stationary scatterers, but it represents a process of low-pass filtering in which the compounded echoes from fast-moving objects are suppressed. Ekroll et al ("On the Accuracy of Coherent Compounding Doppler Imaging," *IEEE International Ultrasonics Symposium*, pp. 1730-1733, 2014) have shown the attenuating effect of this filtering on high velocity scatterers and the resulting bias on velocity estimates. An additional drawback of compounding is that the HRI frame rate is reduced to PRF/N, thereby reducing the (slow-time) Nyquist frequency, so aliasing can occur for the already attenuated fast objects. Compounding is nevertheless necessary in existing techniques to improve the beam profile of the LRI frames in order to suppress off-focus or out-of-cell echoes and produce high-resolution frames. If the total transmit angle swing is $\Delta\alpha$, then the angle increment is $\Delta\alpha/N$. Increasing N reduces the angle increment, thereby improving the beam profile, but it reduces the slow-time sampling rate and hence the unaliased Doppler frequency limit. Hence, a tradeoff exists between the unaliased Doppler limit and the beam profile.

Accordingly, there is a continuing need for alternative Doppler flow measurement systems and methods.

SUMMARY OF THE INVENTION

In an aspect there is provided, a Doppler shift flow measurement system comprising:
a random generator outputting a control signal encoding a random selection;
an ultrasonic array transducer for emitting a sequence of transmit pulses at a target and for receiving an echo of each transmit pulse reflected from the target, each transmit pulse independently adjusted to an adjustable steering angle corresponding to a unique random selection so that the sequence of transmit pulses is a random sweep;
a memory for storing echo data;
a processor connected to the memory for using the echo data to extract a Doppler parameter; and
a display for providing a visual representation of the Doppler parameter.

In another aspect there is provided, a Doppler shift flow measurement system comprising:
a random generator outputting a control signal encoding a random selection;
an ultrasonic array transducer for emitting a sequence of transmit pulses at a target and for receiving an echo of each transmit pulse reflected from the target, each transmit pulse applied to a selectable transducer element or virtual source corresponding to the random selection, each transmit pulse independently applied to the selectable transducer element or virtual source corresponding to a unique random selection so that the sequence of transmit pulses is a random sweep;
a memory for storing echo data;
a processor connected to the memory for using echo data to extract a Doppler parameter; and
a display for providing a visual representation of the Doppler parameter.

In yet another aspect there is provided, a Doppler shift flow measurement system comprising:
a random generator outputting a control signal encoding a random selection;
an ultrasonic array transducer for emitting a sequence of transmit pulses at a target at either an adjustable steering angle (plane wave imaging) or from a selectable transducer array element (synthetic aperture imaging) corresponding to the random selection and for receiving an echo of each transmit pulse reflected from the target, where each transmit pulse is independently adjusted to a steering angle (plane wave imaging) or transducer array element (synthetic aperture imaging) corresponding to a unique random selection so that the sequence of transmit pulses is a random sweep;
a memory for storing echo data; and
a processor connected to the memory for using echo data to extract a Doppler parameter;
a display for providing a visual representation of the Doppler parameter.

In further aspects, methods of Doppler flow measurement and computer-readable medium incorporating the same are also provided.

selectable transducer array element or virtual source

DETAILED DESCRIPTION OF PREFERRED EMBODIMENTS

Figure 1:
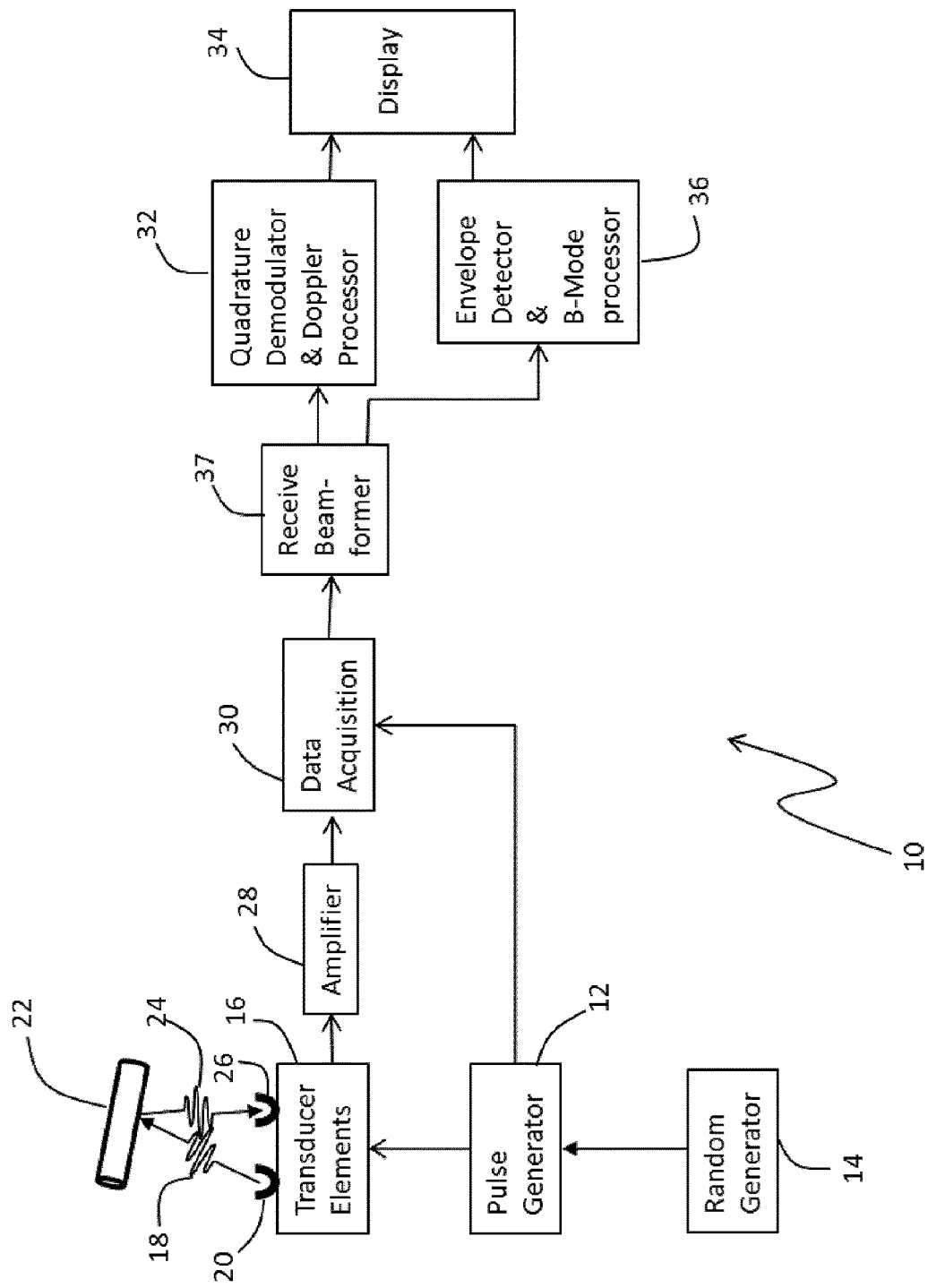
FIG. 1 shows a block diagram view of a Doppler flow measurement system.

Referring to the drawings, a Doppler flow measurement system and method is now described.

FIG. 1 shows a block diagram schematic view of a Doppler flow measurement system 10. The Doppler flow measurement system employs the Doppler effect to determine parameters to characterize flow of a fluid or motion or deformation of a tissue. The system 10 comprises a pulse generator source 12 for outputting pulsed electrical signals that are communicated to transducer 16. Transducer 16 includes multiple elements and is configured to convert pulsed electrical signals into ultrasonic pulses. Transducer 16 emits an ultrasonic transmit pulse 18 from a transmitter element 20 towards a target sample 22. The transducer 16 is also configured to receive and capture a backscattered echo 24 from the target sample 22 at a receiver element 26. The multiple elements of the transducer 16 are each configured to both transmit and receive. In a typical transmit/receive cycle, the ultrasonic transmit pulse is transmitted from one or more elements and the echo is received by one or more elements.

In the case of plane wave imaging, the selection of the transmit tilt angle for each ultrasonic transmit pulse 18 is controlled by a random generator 14. Random generator 14, such as a linear feedback shift register, outputs a control signal to pulse generator 12 at the start of each new transmit/receive cycle to randomly select a transmit tilt angle for the ultrasonic transmit pulse 18. Over a plurality of transmit/receive cycles the random generator results in a non-linear, and more specifically a randomized sequence of transmit tilt angles, and a corresponding non-linear sequence of transmit pulses in a randomized sweep. The random generator can take any convenient form including, for example, algorithmic selections produced in real-time or selections from one or more sets of predetermined pseudo-random sequences.

Once the backscattered echo 24 from target 22 is captured by the receiver element 26, the echo is reconverted to an electrical signal and if needed amplified by amplifier 28 and communicated to a data acquisition module 30, which converts the electrical analog signals into digital data or signals. The data acquisition module 30 also receives the electrical signal corresponding to the ultrasonic transmit pulse 18 for controlling and adjusting the converted electrical signals of the backscattered echo 24. The data acquisition module is operably connected with both memory and processors (not shown) so as to store input data and signal processing results. The receive beamformer 37 applies a mathematical formula to a multitude of digital signals acquired from the data acquisition module 30 in order to improve the image resolution. Each digital signal is received from a distinct transducer receive element 26, amplified by the amplifier module 28, and acquired by the data acquisition module 30. The Doppler processor 32 performs quadrature demodulation of the acquired and beamformed digital data provided by the beamformer 37, accumulates data from a plurality of transmit receive cycles to generate a Doppler ensemble that is used for estimating various Doppler flow parameters such as flow velocity, power, direction . . . etc. From the estimated flow parameters, the Doppler processor then assembles flow images that are presented to the display module 34 for visual display. In parallel, the B-mode processor 36 performs envelope detection on the beamformed digital signals presented by the beamformer 37 and assembles a brightness mode (B-mode) image for the display module 34, which applies mathematical formulas to combine the B-mode images with the flow images.

Figure 2:
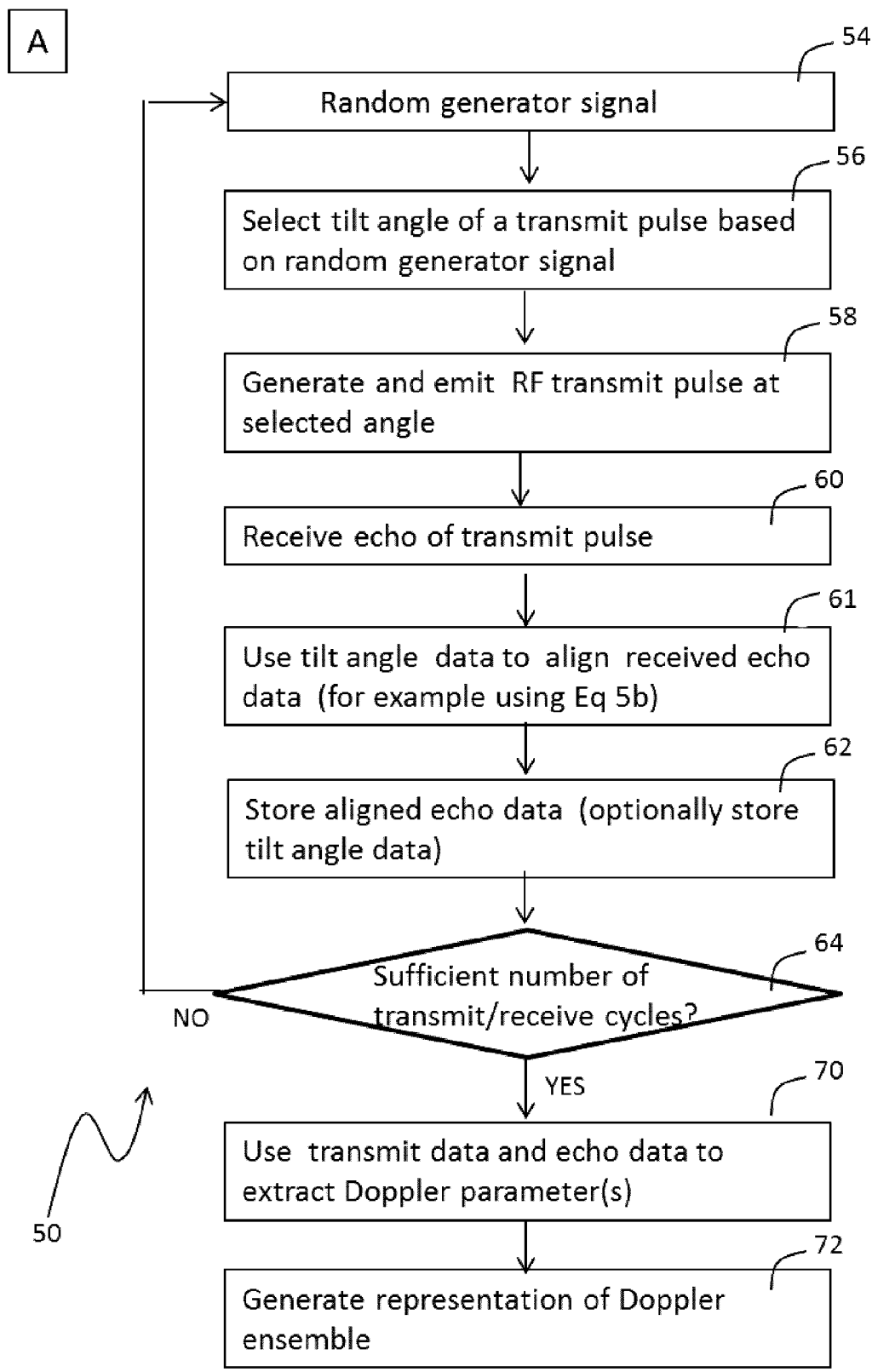
FIG. 2 shows flow diagrams for several variants of a Doppler flow measurement method.
Figure 2:
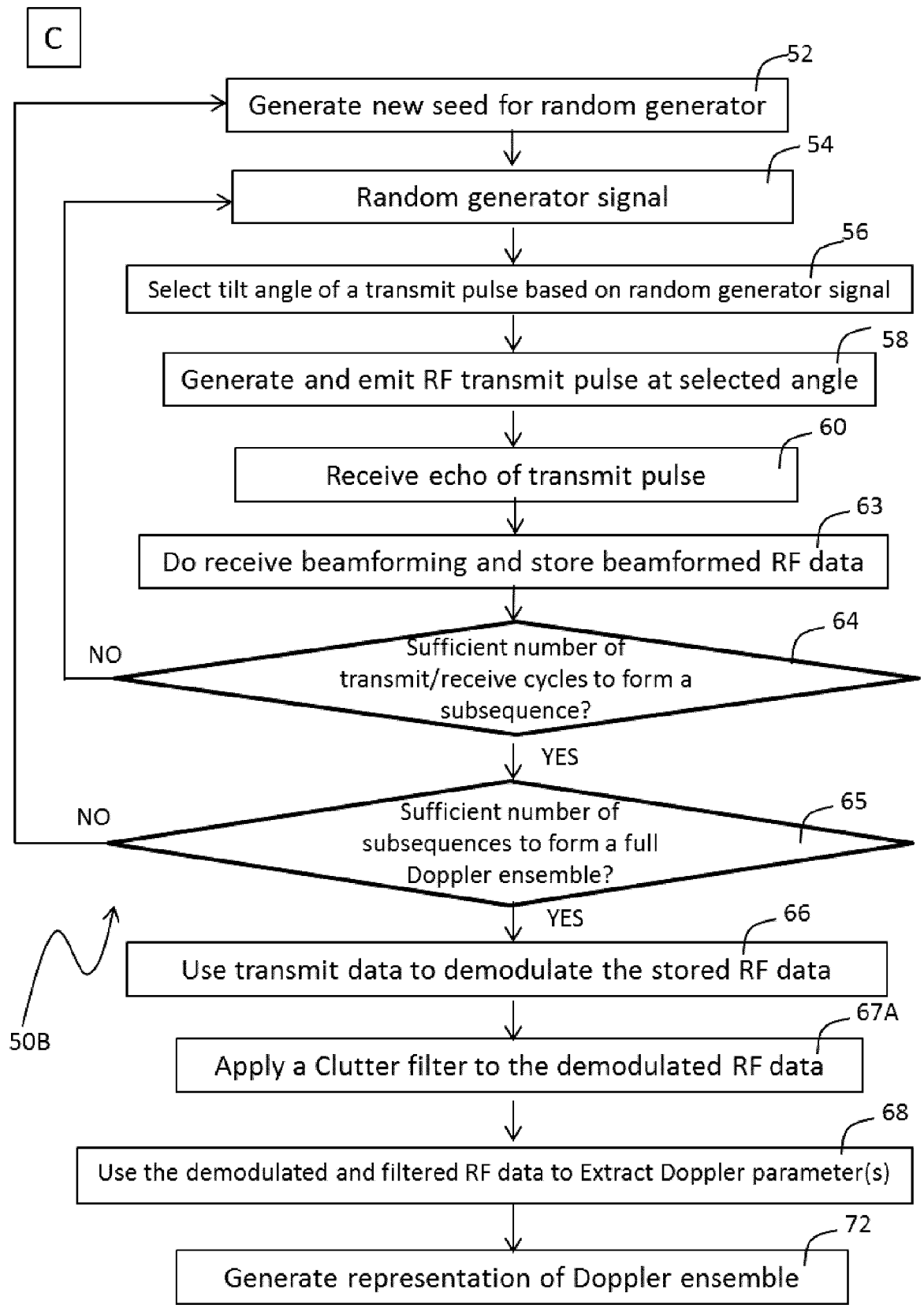
Figure 2:
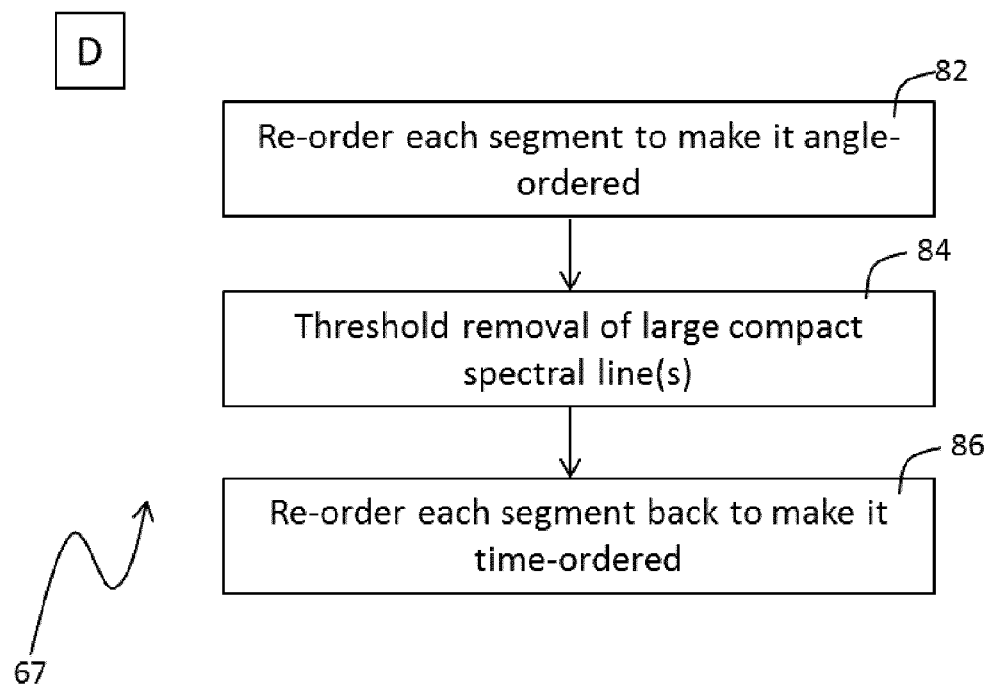
Figure 2:
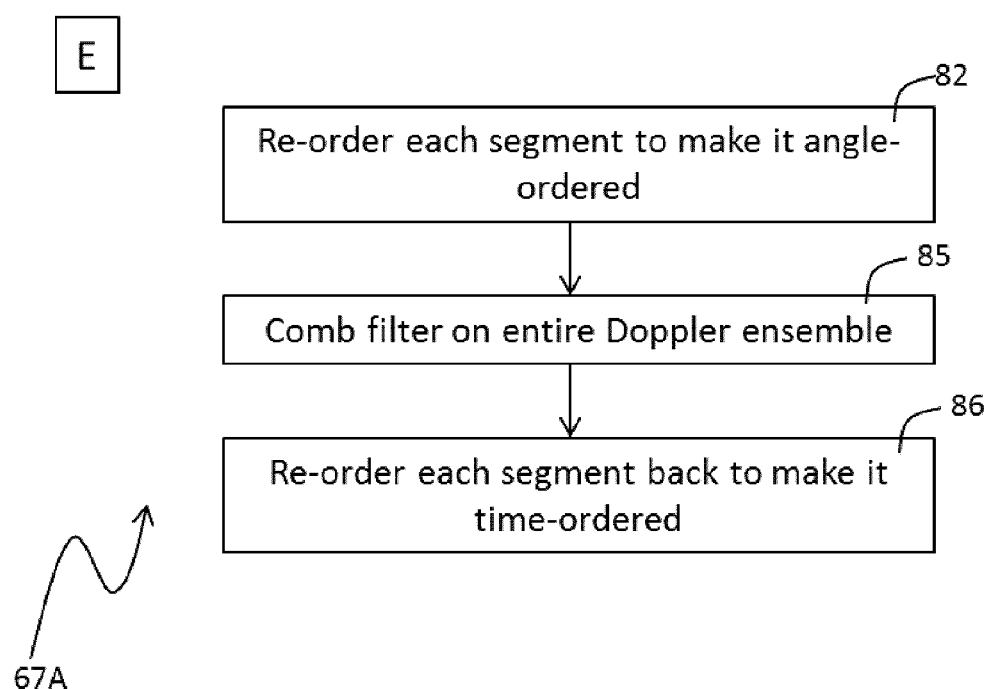

FIG. 2A shows a flow chart diagram of an illustrative Doppler flow measurement method 50. The method 50 comprises a plurality of transmit/receive cycles and processing of data obtained from the plurality of transmit/receive cycles to yield a diagnostic result. Each transmit/receive cycle begins with a random or pseudo-random generator executing a randomizing algorithm and outputs a random generator signal 54. Alternatively, the random generator signal may be selected from a predetermined randomized sequence instead of executing a randomizing algorithm within each transmit/receive cycle/loop. The random generator signal is received by a pulse generator which generates an electrical signal pulse for communication to an ultrasound transducer for emission of a transmit pulse. More specifically, prior to emission of each transmit pulse, the pulse generator generates the electrical signal pulse that corresponds to the random generator signal 54, and the electrical signal pulse, modified by the random generator signal, is communicated to the transducer. The electrical signal pulse is received by the transducer providing a corresponding tilt angle of the transmit pulse 56. The tilt angle of the transmit pulse is adjusted from a default angular position to a selected angular position that corresponds to the random generator signal 54. Adjusting the tilt angle to match the random generator signal 54 and its corresponding electrical signal pulse, the transducer emits the corresponding transmit pulse 58 directed towards a target sample. The transducer also receives and captures an echo of the transmit pulse from the target sample 60. The transmit pulse tilt angle data can then be used to align the received echo data 61 to improve image resolution (for example using Equation 5b described below). The aligned echo data can be stored in memory 62, and if desired the tilt angle data may also be stored in memory. Alternatively, the alignment of echo data may occur after exiting from the transmit/receive cycles with the transmit pulse data and the echo data stored in memory for later comparison once sufficient data is obtained from a sufficient number of transmit/receive cycles. A decision to exit looping of transmit/receive cycles may be based on a predetermined number that can be set according to a desired implementation and/or a desired diagnostic user interface 64. Alternatively, a decision to exit looping of transmit/receive cycles may be based on a preliminary analysis of stored transmit pulse and echo data to determine whether a predetermined threshold or criteria has been reached. Upon acquiring sufficient data from the plurality of transmit/receive cycles, the data is processed to quantify a relevant Doppler parameter 70 and generate a representation that indicates a diagnostic result 72.

Many different signal processing techniques for analyzing radio frequency (RF) data are conventionally available. More specifically, many signal processing technique are recognized as providing improved resolution for ultrasound imaging. Such signal processing techniques can optionally be included to enhance resolution of images produced using the method 50 shown in FIG. 2A. For example, as shown in FIG. 2B, a receive beamforming step 63 can be applied to the received echo data 60 to focus the echo data signal and the beamformed echo data can be stored in memory. The receive beamforming step 63 includes an alignment of echo data and therefore can replace the steps of aligning received echo data 61 and storing the aligned echo data 62 shown in FIG. 2A. In addition to receive beamforming, further signal processing techniques such as demodulation 66 and filtering 67 may be applied to stored beamformed echo data. Demodulation of the stored echo data 66 can include quadrature demodulation resulting in I/Q data or frames. Quadrature demodulation and signal processing using In-phase component (I) and Quadrature component (Q) is well developed in the field of ultrasound imaging, and any such suitable demodulation technique may be used. A clutter filter can be applied to the demodulated echo data to reduce or suppress signals from off-focus objects 67. As with beamforming techniques and demodulation techniques, clutter filters are also an active area of technology development that has been used in ultrasound imaging. Suitable clutter filters may be incorporated as desired depending on the specific implementation of the system or method. Subsequent to treatment with a clutter filter the filtered echo data can be analyzed to calculate a Doppler parameter 68 and generate a representation of the Doppler ensemble 72, such as a color Doppler image.

FIG. 2D shows processing steps of a suitable clutter filter 67 that can be incorporated in the method 50A shown in FIG. 2B. Clutter filter 67 may be a time-shuffling clutter filter (TCF) as described in greater detail below. The TCF rejects stationary clutter in spread-spectrum Doppler beamforming. In the transmit/receive cycling data is acquired using a random sequence of plane-wave tilt angles to form a time-ordered Doppler ensemble whose frequency spectrum has the in-cell echoes represented with compact bandwidth and its out-of-cell clutter echoes spread over the entire spectrum and look noise-like. The ensemble is then reordered to form an angle-ordered signal 82, i.e. samples are the result of a linearly increasing plane-wave tilt angle, and hence the timing of each sample is now shuffled and thus randomized. As a result, the clutter is spectrally compacted whereas the in-cell echoes are spectrally spread. The TCF method then uses thresholds in the frequency domain of the angle-ordered signal to remove large compact spectral lines 84, thereby suppressing clutter, and finally re-ordering the samples back to form the time-ordered filtered signal ensemble 86.

FIGS. 2C and 2E provide another example of a useful clutter filter that includes reordering of the Doppler ensemble. As shown in FIG. 2C, method 50B comprises an internal loop that corresponds to the transmit/receive cycle shown in FIG. 2B, except that a sufficient plurality of the transmit/receive cycles combine to form a subsequence 64A. In turn, a plurality of subsequences combine to form the overall randomized sequence 65 to form the Doppler ensemble. The internal loop (steps 54 to 64A) is controlled by an external loop that provides a new seed for random generation of a subsequence with external loop completion and exit dependent on attaining a sufficient number of subsequences to form a Doppler ensemble 65. As described for method 50, any convenient method of random generation may be incorporated including, for example, algorithmic selections produced in real-time or selections from one or more sets of predetermined pseudo-random sequences. For example, where selections are made from predetermined sets or tables of randomized sequences, step 52 can be a selection of a next seed in a predetermined pseudo-random sequence and step 54 can be a selection of a next entry for the selected seed.

Method 50B includes a clutter filter 67A that is a periodic time-shuffling clutter filter (PTCF) useful for suppressing most types of stationary echoes such as vessel wall or tissue clutter. PTCF is described in greater detail below. Briefly, as with RCF, PRCF uses a random sequence of plane-wave tilt angles to form a Doppler ensemble, but it divides the sequence into smaller segments, all using the same set of tilt angles, but each with its own unique random subsequence. As a result, the angle-ordered ensemble 82 of stationary signals is periodic and occupies discrete spectral components at well-defined locations, which can be cleared by applying a comb filter 83 and without the need for thresholds or threshold calibration. The suppression of discrete spectral components minimally affects the in-cell or blood Doppler signal since it is spread over the entire angle-ordered spectrum. Additionally, the segmented sweep allows retrospective selection of the Doppler ensemble size for a Doppler parameter quantification such as velocity estimation.

The Doppler flow measurement system and method have been mathematically validated. Mathematical analysis described in the following paragraphs shows that, for each point in a field of view, scatterers inside the resolution cell produce echoes that have consistent phase at each transmit angle, whereas scatterers outside the resolution cell produce echoes with random phase due to the random sequence of transmit steering angles. This random phase spreads the spectrum of the echoes from off-focus objects, thereby suppressing those objects and eliminating their effect from Doppler signal parameter estimates. In contrast, the linear sweep of transmit angles used in conventional plane-wave imaging results in off-focus scatterers producing slow-time signals with frequencies that depend on their lateral position. These off-focus tones make compounding necessary to suppress them. The following mathematical analysis is for illustration purposes only, without wishing to be bound by theory, and is not intended to be a limiting description.

Figure 3:
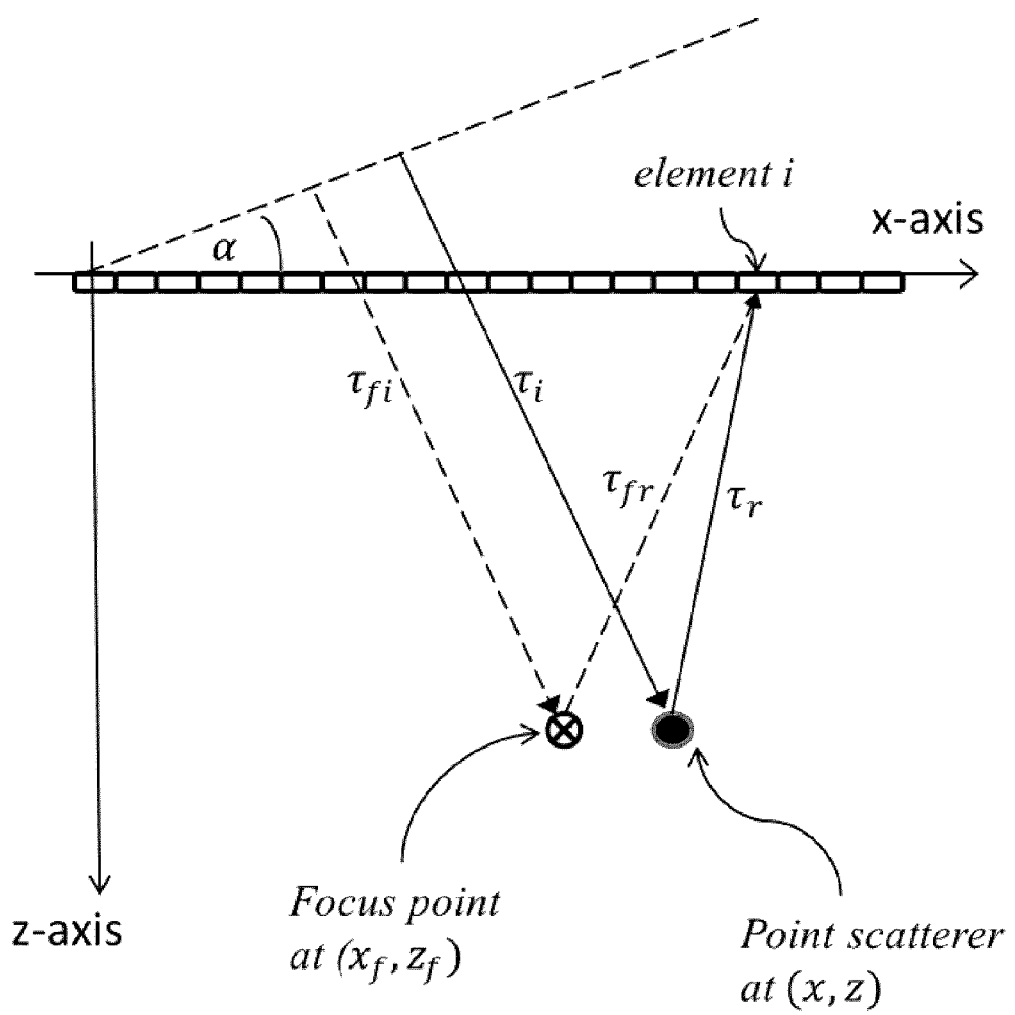
FIG. 3 shows imaging geometry for an array transducer transmitting a plane wave at an angle α, an off-focus point scatterer, and the focal point with the lengths of the rays along transmit and receive directions representing the one-way transit times for an in-focus echo (dashed lines) and an off-focus echo (solid lines), respectively.

Mathematical Analysis: Echoes from a Single Plane-Wave Pulse. In an image scene isonified with a single plane-wave pulse from a tilt angle α, the pressure waveform transmitted from the leftmost element of the transducer array will be:

$$p_0(t) = G(t)\cos(\omega t) = G(t)\frac{e^{j\omega t} + e^{-j\omega t}}{2}, \quad (1)$$

where G(t) is the pulse envelope and the t=0 time reference is taken with respect to the middle of the pulse envelope fired from the element on the left edge of the array (FIG. 3). The positive frequency component of $p_0$ can be written as:

$$p_0^+(t) = G(t)e^{j\omega t} \quad (2)$$

For simplicity of notation, the positive-frequency component is examined here, knowing that the negative-frequency component will be conjugate symmetric to the positive-frequency component. Using the coordinate system defined in FIG. 3, the normalized pressure incident at a scatterer located at a point (x, z) is:

$$p(\alpha,x,z,t) = G(t-\tau_i(\alpha))e^{j\omega(t-\tau_i(\alpha))} \quad (3)$$

where $$\tau_i(\alpha, x, z) = \frac{z\cos\alpha + x\sin\alpha}{c}$$

is the transit time for the incident pressure wave to reach the scatterer. The radio-frequency (RF) signal received by transducer element m due to the single scatterer is:

$$RF(\alpha,m,t,x,z) = G(t-\tau_i(\alpha,x,z)-\tau_r(m,x,z))e^{j\omega(t-\tau_i(\alpha,x,z))}e^{-j\omega\tau_r(m,x,z)}. \quad (4)$$

where $$\tau_r(m, x, z) = \frac{\sqrt{(x-md)^2 + z^2}}{c}$$

is the transit time for the scattered wave to reach the transducer element, m=0 denotes the leftmost element, and d is the array's element pitch. Note that the scattering coefficient of the point scatterer has been absorbed, without any loss of generality, into G(t).

In delay-and-sum receive beamforming with a linear array, a focus at a point ($x_f, z_f$) is created by delaying the RF signals from the elements of an aperture centered at position $x_f$ such that the echo received from a scatterer at the focus by all of the elements is aligned at the same time, $t=2z_f/c$. Hence, the RF signal at each element m is delayed by:

$$\tau_f(\alpha, m, x_f, z_f) = \tau_{fi}(\alpha, x_f, z_f) + \tau_{fr}(m, x_f, z_f) - 2z_f/c, \quad (5a)$$

where $$\tau_{fi}(\alpha, x_f, z_f) = \frac{z_f\cos\alpha + x_f\sin\alpha}{c}, \quad (5b)$$

$$\tau_{fr}(m, x_f, z_f) = \frac{\sqrt{(x_f - md)^2 + z_f^2}}{c}. \quad (5c)$$

Hence, the output of the receive beamformer is:

$$bfRF(\alpha, x_j, z_j, x, z, t) = e^{j\omega t}e^{-j\omega(\tau_i - \tau_{fi} + 2z_f/c)} \sum_{m=l-a}^{l+a} G(t - \tau_i - \tau_r + \tau_{ji} + \tau_{jr} + 2z_j/c)e^{-j\omega(\tau_r - \tau_{fr})}, \quad (6)$$

where $x_f = ld$, l is the scanline, l=0 denotes the leftmost scan line, and 2a+1 is the number of elements in the receive aperture. The quadrature demodulated baseband signal is then:

$$bb(a, x_j, z_j, x, z, t) = \\ e^{-j\omega(\tau_i - \tau_{fi} + 2z_f/c)} \sum_{m=1-a}^{i+a} G(t - \tau_i - \tau_r + \tau_{fi} + \tau_{fr} + 2z_f/c) e^{-j\omega(\tau_r - \tau_{fr})}. \quad (7)$$

A low-resolution image can be reconstructed from the baseband signals by applying the receive focusing delay at every pixel in the image and sampling at $t=2z_f/c$:

$$LRI(\alpha, x_f, z_f, x, z) = B(\alpha, x_f, z_f, x, z) e^{-j\omega(\tau_i - \tau_{fi})}, \quad (8)$$

where the term inside the summation and the term $e^{2z_f/c}$ have been both absorbed into the function B, which represents the beam profile at $(x_f, z_f)$. Substitution for $\tau_i$ and $\tau_{fi}$ in (8) yields:

$$LRI(\alpha, x_f, z_f, x, z) = B(\alpha, x_f, z_f, x, z) e^{-jk[(z-z_f)\cos\alpha + (x-x_f)\sin\alpha]}. \quad (9)$$

Mathematical Analysis: Echoes from Multiple Plane-Wave Pulses. If N plane-wave pulses are emitted at a pulse-repetition interval, PRI, such that each emission has a tilt angle $\alpha(n)$ drawn from a sequence $\{\alpha_{-N/2}, \ldots \alpha_{-1}, \alpha_0, \alpha_1, \ldots \alpha_{N/2-1}\}$, and if the point scatterer is moving with a velocity $(v_x, v_z)$, then its displacement from the focal point is $$(x_0 + nPRI v_x, z_0 + nPRI v_z),$$

where n is the pulse number and spans the range $-N/2$ to $N/2$, and $(x_0, z_0)$ is the scatterer's position relative to the focus at the middle of the sweep, i.e., $$z_0 = [x - x_f]_{\alpha = \alpha_0} \text{ and } z_0 = [z - z_f]_{\alpha = \alpha_0}.$$

Under these conditions, (9) becomes:

$$LRI(\alpha(n), x_f, z_f, x, z) = B(\alpha(n), x_f, z_f, x, z) \\ e^{-jk[(z_0 + nPRI v_z)\cos\alpha(n) + (x_0 + nPRI v_x)\sin\alpha(n)]} \quad (10)$$

For small tilt angles, the approximations $\cos(\alpha) \approx 1$ and $\sin(\alpha) \approx \alpha$ apply, hence the term $$e^{-31 jkz_0 \cos(\alpha(n))} \approx e^{-jkz_0},$$

which is a constant, and:

$$LRI(\alpha(n), x_f, z_f, x, z) = C(\alpha(n), x_f, z_f, x, z) \\ e^{-jk(nPRI v_z + x_0 \alpha(n) + nPRI v_x \alpha(n))} \quad (11)$$

where $C = Be^{-jkz_0}$. For the case of a linear transmit angle sweep, $\alpha(n) = n\delta$, where $\delta = \Delta\alpha/N$ is the transmit angle increment, and (11) becomes:

$$LRI(\alpha, x_f, z_f, x, z) = C(\alpha, x_f, z_f, x, z) e^{-jkPRI v_z n} e^{-jkx_0 n\delta} \\ e^{-jkPRI v_x n^2 \delta} \quad (12)$$

Note that in (10) to (12), a, x and z are functions of n; hence C is also a function of n and it acts as a time-windowing function that is different for each scatterer depending on its starting position and velocity.

Mathematical Analysis: Stationary Scatterers: For stationary objects, substitution of $v_x = 0$ and $v_z = 0$ into (12) yields:

$$LRI(\alpha(n), x_f, z_f, x, z) = C(\alpha(n), x_f, z_f, x, z) e^{-jkx_0 n\delta} \quad (13)$$

Equation (13) shows that the slow-time signal from an off-focus stationary scatterer will be sinusoidal, with a frequency that increases with the object's lateral distance from the focus, and that frequency aliasing occurs when:

$$x_0 \geq \frac{2\pi}{k\delta} = \frac{\lambda}{\delta} \quad (14)$$

Hence, to ensure the grating lobes are outside the imaging scene, whose width is the same as the array width L, the angle step, $\delta$, must be smaller than $L/\lambda$. FIG. 4A shows amplitude normalized plots of (13) for stationary scatterers that are laterally displaced from the focal point by different distances. The plot excludes the windowing function $C(\alpha(n), x_f, z_f, x, z)$. FIG. 4B shows a wire phantom imaged using the same sweep parameters as in FIG. 4A. The B-mode HRI frame was produced by averaging all of the LRI frames from the different tilt angles, which is equivalent to computing bin 0 of the fast Fourier transform (FFT) for each pixel's slow-time signal. FIG. 4C shows the FFT of slow-time signals from different lateral focus positions on the phantom, the first being the exact position of the wire. The FFT magnitude of the slow-time signal decreases as the focus moves away from the wire's actual position due to the receive beamforming. FIG. 4D shows a normalized plot that removes the beamforming attenuation for better visualization of the spectral peaks.

Figure 4:
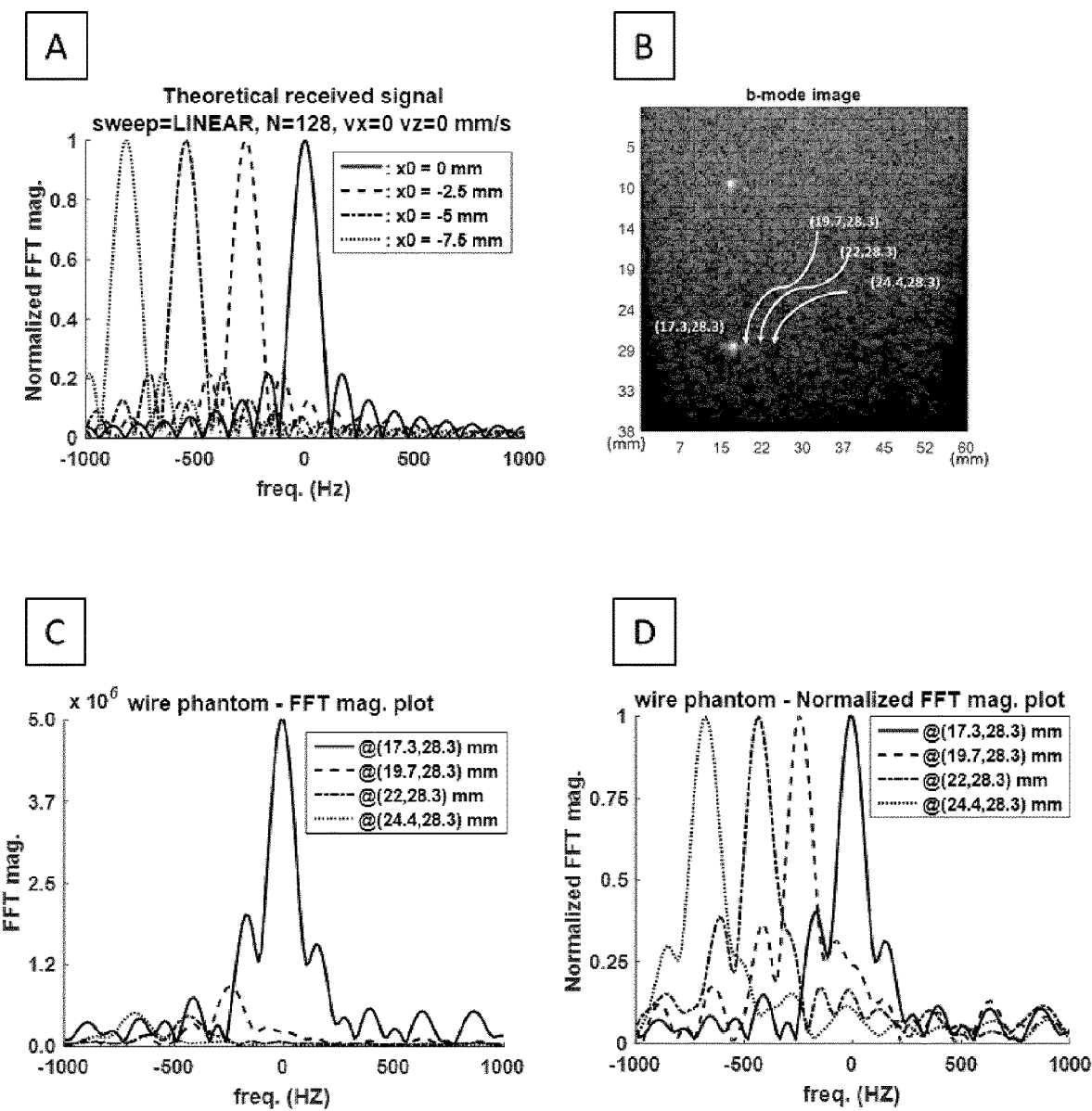
FIG. 4 shows (a) theoretical normalized FFT plots of eq (13) for a linear sequence of plane-wave tilt angles with center frequency f 0=5 MHz, PRF=15 kHz, transmit angles $-8.192^c<\alpha<8.192^c$, transmit angle step $\delta=0.512^c$, and ensemble length of N=32, with waveforms representing signals from point scatterers at different lateral positions relative to the focus point; (b) B-mode image of a wire phantom showing the location of a wire at (17.3, 28.3) mm and the locations of three other pixels displayed for comparison in panels (c) and (d); the sweep used the same parameters as in the theoretical plot (a); the B-mode image was formed by averaging 128 low-resolution frames; (c) FFT of slow-time signals for the 4 pixels shown in (b); the signal level decays as the sample position moves away from the wire due to the receive beam pattern; and (d) Normalized FFT of the slow-time wire phantom signals, which removes the signal level decay for better visualization.
Figure 5:
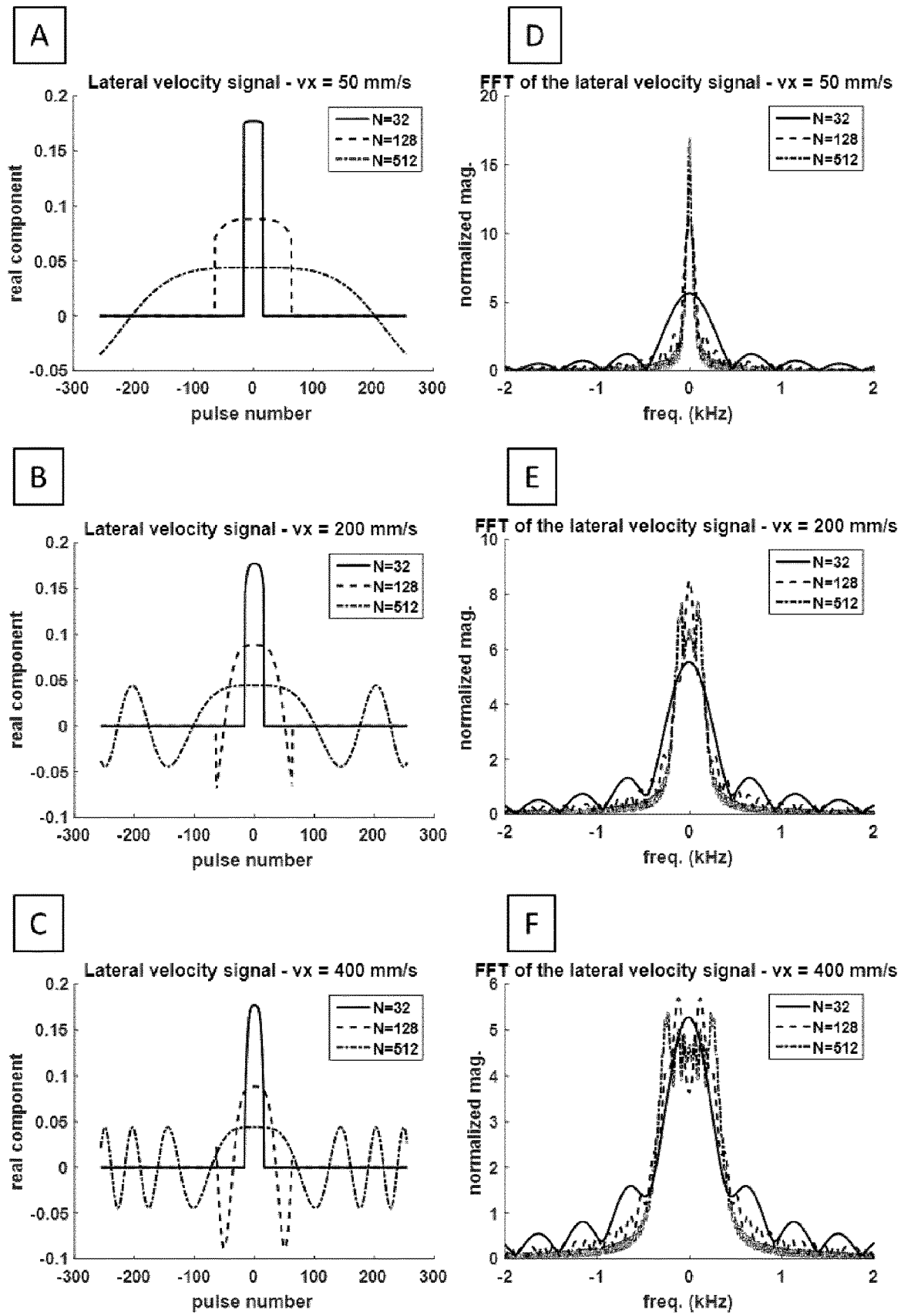
FIG. 5 shows theoretical normalized lateral velocity signal components (left column), and corresponding Doppler spectra (right column) for 3 different scatterer velocities: (a, d) 50 mm/s, (b, e) 200 mm/s and (c, f) 400 mm/s, each measured with sweep lengths of 32, 128, and 512 pulses and plots generated by evaluating eq (12) for the same combination of transmit parameters used in FIG. 4, with increasing sweep lengths.

Mathematical Analysis: Moving Scatterers. For moving objects, Eqn. (12) applies. The expression is a product of three exponential components and can be viewed as three separate signals that are inter-modulated. The first signal represents a tone with a Doppler-shifted frequency that is a function of the scatterer's axial velocity, $v_z$. The second signal represents a tone whose frequency is a function of the scatterer's lateral position, $x_0$. The third signal has a quadratic term inside the exponent and represents a chirp that is a function of the scatterer's lateral velocity, $v_x$. The Fourier transform of the combined signal is hence expected to be that of a time-windowed chirp that is frequency shifted due to the Doppler and lateral position frequency shifts. FIG. 5 shows a plot of the lateral velocity (chirp) signal using the same transmit parameters as FIG. 4 but for different values for N and $\delta$. Note that the signals are normalized to have unit power, so the shorter transmit sequences have larger amplitudes in the time domain. Even for high lateral velocities of 400 mm/s, which can be reached inside the aorta or carotid arteries, increasing the number of plane wave angles, N, does not significantly change the bandwidth of the chirp signal, but rather reduces the signal strength, and makes the shape of the spectrum more complex. The bandwidth is primarily dictated by the lateral velocity. Comparison of FIG. 5F to FIG. 4A shows that, for this example's transmit parameters, the lateral velocity component has a less significant effect on the central frequency of the slow-time signal than does the lateral position component. Note that all sweeps in these examples have the same transmit angle swing $\Delta\alpha = \alpha_{max} - \alpha_{min}$, so the angle increment $\delta = \Delta\alpha/N$ is smaller for the longer sequences.

Mathematical Analysis: Clutter Filtering. With existing Doppler imaging methods, to increase the image resolution and form an HRI frame, echoes from off-focus scatterers (i.e., clutter) need to be suppressed. For stationary or slow-moving objects, the desired signal from in-focus objects is mostly comprised of the lateral position tone, which is at or close to 0 Hz, whereas the clutter signal has a frequency that increases with the scatterer's lateral position relative to the focus as illustrated in FIG. 4A. Clutter filtering can be defined in the context of beamforming as the suppression of signals from scatterers that are outside the resolution cell and can be achieved by coherently summing the N LRI frames to form a single HRI frame. Applying this process of compounding to (13) yields:

$$HRI(x_f, z_f, x, z) = \sum_{n=-\frac{N}{2}}^{\frac{N}{2}-1} C(\alpha(n), x_f, z_f, x, z)e^{-jkx_0 n\delta} \approx \quad (15)$$

$$C(\alpha_0, x_f, z_f, x, z)e^{jk\delta x_0/2} \frac{\sin\left(\frac{\pi x_0 N\delta}{\lambda}\right)}{\sin\left(\frac{\pi x_0 \delta}{\lambda}\right)}$$

whereas (15) assumes a monochromatic plane-wave where the magnitude of the windowing function C doesn't change much with the tilt angle. For scatterer positions near the focus, (15) can be approximated by:

$$HRI(x_f, z_f, x, z) \approx C(\alpha_0, x_f, z_f, x, z)Ne^{jk\delta x_0/2}\operatorname{sinc}\left(\frac{\pi x_0 N\delta}{\lambda}\right) \quad (16)$$

which is the response of a decimating mean filter applied to the slow-time signal from (x, z). This filter keeps the tone corresponding to $x_0=0$ while suppressing all the other tones that constitute the clutter. The numerator of (15) shows that the resolution is improved (i.e., the main lobe width becomes narrower) by increasing the angle swing $\Delta\alpha=N\delta$, whereas the denominator and (14) show that grating lobes get closer by increasing the angle step $\delta$, thus raising the sidelobes.

For moving scatterers, the in-focus slow-time signal is shifted away from 0 Hz due to the Doppler frequency shifts. Suppression and aliasing of the slow-time signal from a moving scatterer may occur when the Doppler shift is above the Nyquist limit, which is half the HRI frame rate. Hence, with current methods, a trade-off exists between improved beam profiles using a large number of plane-wave angles and higher unaliased Doppler frequencies from the use of higher HRI frame rates, which require a lower number of transmit angles.

Mathematical Analysis: Spread-Spectrum Method. The spread-spectrum method provided herein is a method of spreading the clutter spectrum such that it appears as random noise, thereby reducing its peak power, while keeping the in-focus signal intact. When the spreading is sufficient, it can eliminate the need for compounding, and as a result high spatial resolution and high unaliased Doppler frequencies can be obtained simultaneously.

If a uniformly distributed pseudo-random sequence PN(n) drawn from the range [−N/2, N/2−1] to select the plane wave transmit angles is used, then α(n) is also a pseudo-random sequence:

$$\alpha(n)=PN(n)\delta \quad (17)$$

The pseudo-random sequence may be generated using a linear feedback shift register. Substitution for α(n) in (11) yields:

$$LRI(\alpha(n), x_f, x, z) = C(x_f, x, z)e^{-jkPRI v_z n} \\ e^{-jkx_0\delta PN(n)}e^{-jkPRI v_x \delta PN(n)n} \quad (18)$$

Figure 6:
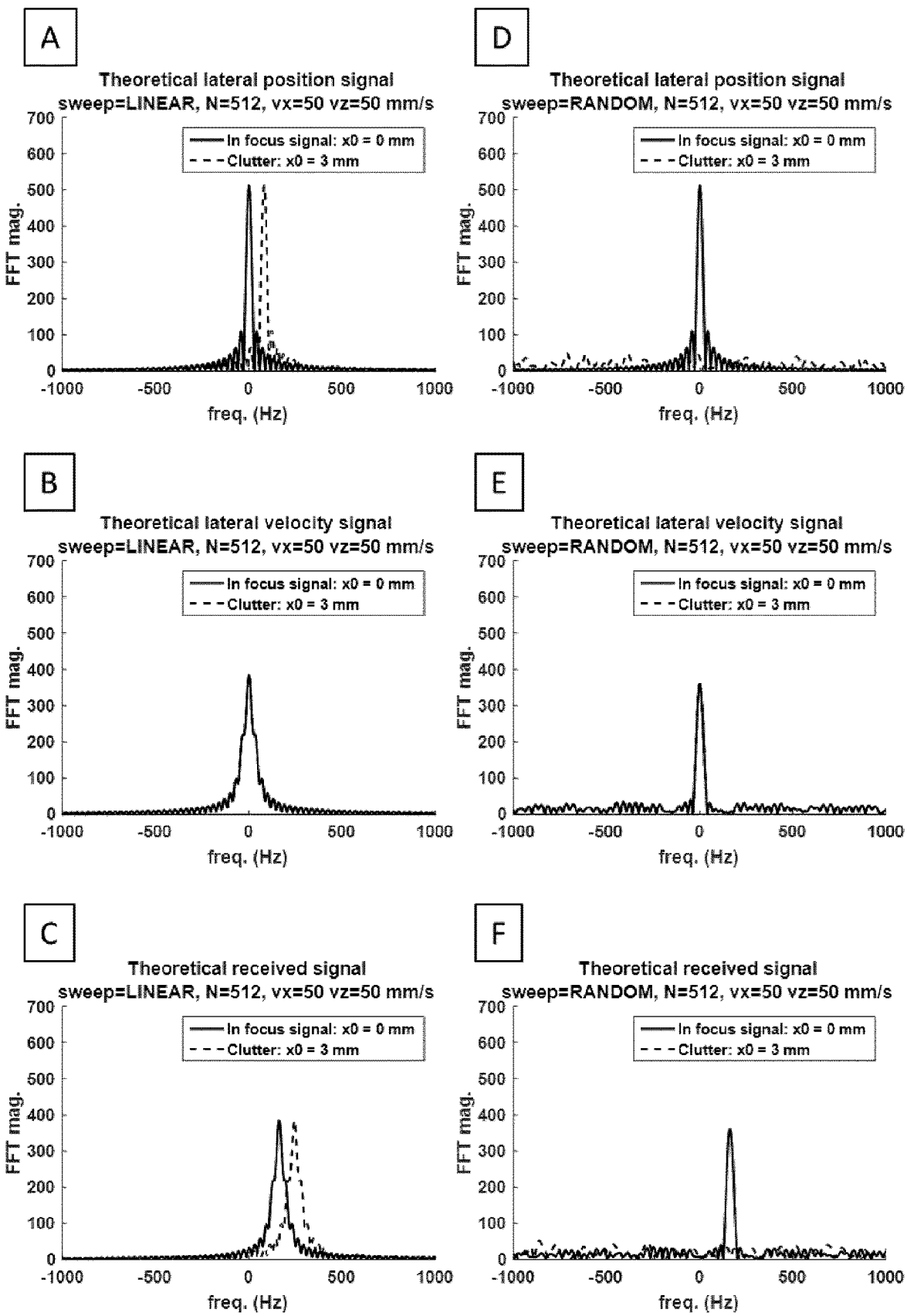
FIG. 6 shows theoretical Doppler spectra obtained using a 512-pulse transmit-angle sweep using a linear (left column) and random (right column) sequence. Panels show corresponding lateral position component of in-focus (solid line) and clutter (dashed line) signals (a, d), lateral velocity component of in-focus and clutter signals (b, e), and complete Doppler spectra of in-focus and clutter signals (c, f).

Since the system is linear, (17) can be applied individually to in-focus and clutter scatterers. FIG. 6 shows an overlaid plot of (17) for two objects, an in-focus scatterer and an off-focus (clutter) object located a lateral distance of 3 mm from focus. The top row shows the signal components for a 512-pulse linear sweep, while the bottom row shows the signal components for an equal length random sweep using the same transmit parameters as in FIG. 4 and FIG. 5. The Doppler component is not plotted since it is a single tone that is similar among sweeps.

As can be seen in (17) and FIG. 6D, the lateral position component has a high degree of spectral spreading for clutter scatterers, so it is readily suppressed, but it still produces an intact tone for in-focus scatterers. Comparing FIG. 6A and FIG. 6D, a linear sweep (FIG. 6A) requires that the clutter be suppressed by some additional means such as a low pass filter (compounding), while a random sweep (FIG. 6D) requires no further processing since the clutter is already spectrally spread and thus suppressed. The suppression occurs because the clutter's lateral position component represents a pseudo-random noise sequence whose symbol rate is equal to the slow-time sample rate (also the PRF), and therefore, the clutter spectrum is spread over the entire digital bandwidth, and the clutter power per frequency bin is significantly reduced and becomes noise-like in the frequency domain, which is where most velocity estimators operate. For linear sweeps, the clutter is usually at a higher frequency than the in-focus signal; nevertheless, frequency-domain filters (such as compounding) may not achieve good separation of signal from clutter when the Doppler shift of the in-focus signal is too close to the clutter's lateral position frequency shift, as illustrated in FIG. 6C.

FIG. 6E shows that the lateral velocity component will have some amount of spreading for both in-focus and clutter signals. The degree of spreading depends on the lateral velocity and the spreading may degrade the signal magnitude; however, the degradation is usually small for the typical velocities and sweep lengths of interest.

Mathematical Analysis: Spread-Spectrum Clutter Suppression. Randomizing the phase of the lateral position signal is responsible for spreading its spectrum, and for maximum spread, the transmit angles should map to a phase variation that is an integer multiple of $2\pi$ to produce uniformly distributed random phase for each sample in the slow-time signal. In this case, the frequency spectrum has a signal suppression ratio of $\sqrt{N}$ (The power suppression ratio N is commonly referred to as the processing gain). Hence, maximum spectral spreading of the lateral position component, and accordingly maximum clutter suppression is achieved when:

$$kx_0 N\delta = 2\pi g, \quad (19)$$

or $$x_0 = \frac{\lambda}{N\delta}g \quad (20)$$

where g is an integer. Note that these values of x, are also the lateral position nulls of (15).

Mathematical Analysis: Additional Clutter Filtering via Time Shuffling (TCF). Since the maximum spread-spectrum suppression gain is equal to $\sqrt{N}$, it amounts to only 27 dB of suppression for a sweep of 512 transmit angles. On the other hand, vessel wall clutter can be 60 dB above the blood signal, so spreading the clutter spectrum may not always be sufficient to suppress the vessel wall echoes. A method for additional clutter filtering is therefore proposed in this section. If, after acquiring data with a random sequence of transmit angles, the ensemble of slow-time samples is reordered such that the transmit angles follow a linear-sequence sweep instead of the random one, the samples of the slow-time signal are now time shuffled. This reordering process is a linear operation, so the in-focus and clutter signals can still be analyzed individually. After time shuffling, (18) becomes:

$$LRI(\alpha(n), x_\beta z_\beta x, z) = C(x_\beta z_\beta x, z) e^{-jkPRIv_z PN(n)}$$
$$e^{jkx_0 \delta n} e^{jkPRIv_x \delta PN(n)n} \quad (21)$$

Time shuffling spreads the Doppler component and compacts the lateral position component, while the lateral velocity component remains unchanged. For stationary or slow-moving clutter such as echoes from the vessel wall, the Doppler shift is small, so Eq (21) predicts a somewhat compact tone with only a small spread due to the lateral velocity component. At the same time, the in-focus signal is spread approximately uniformly across the spectrum.

To clarify this concept, consider a sine wave representing the in-focus slow-time signal and a scrambled sine wave representing clutter. If the slow-time samples are reordered based on Eq (21), then the stationary clutter becomes a single tone, whereas the in-focus signal is now scrambled and has a spectrum like white noise. The wall clutter can then be eliminated by zeroing the first few FFT coefficients above a threshold, with very little effect on the in-focus signal since its spectrum is spread over the entire frequency range. Unscrambling the resulting spectrum returns the signal to the form of Eq (18), but with the wall clutter signal removed. Flow-phantom experimental results presented below show that this clutter filter produces images of reasonable quality.

Following the time-shuffling clutter filter, frequency-domain low-pass filtering can be performed with a cutoff frequency of 1.5 kHz, which is the highest expected Doppler shift in the flow-phantom experiments. The low-pass filter improves the signal-to-noise ratio (SNR) for proper velocity estimation using the Kasai et al. method ("Real-time two-dimensional blood flow imaging using an autocorrelation technique," *IEEE Transactions on Sonics and Ultrasonics*, Vols. SU-32, no. 3, pp. 458-464, 1985). Other velocity estimation methods that do not require this filtering (for example: Kay and Marple, "Spectrum analysis—a modern perspective," *Proceedings of the IEEE*, vol. 69, no. 11, pp. 1380-1419, 1981; Vaitkus and Cobbold, "A comparative-study and assessment of Doppler ultrasound spectral estimation techniques. 1. Estimation methods," *Ultrasound in Medicine and Biology*, vol. 14, no. 8, pp. 661-672, 1988; Vaitkus and Cobbold, "A comparative-study and assessment of Doppler ultrasound spectral estimation techniques. 2. Methods and results," *Ultrasound in Medicine and Biology*, vol. 14, no. 8, pp. 673-688, 1988) may be substituted.

Figure 10:
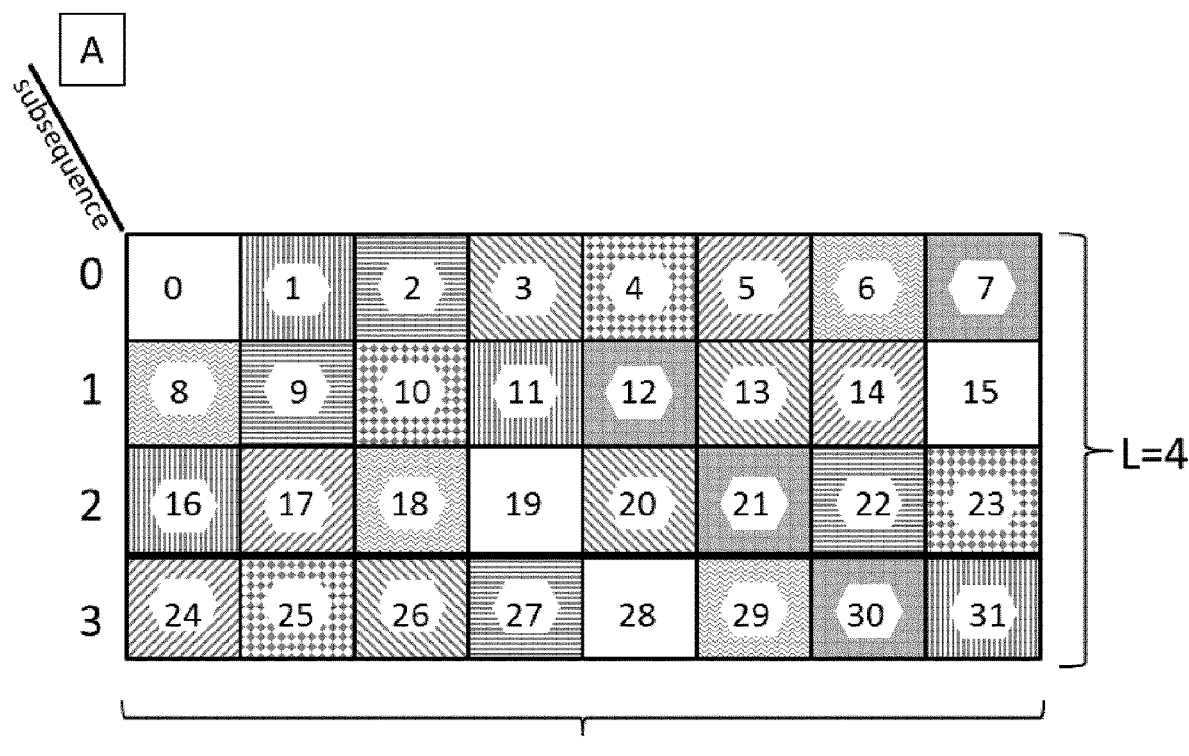
FIG. 10 shows a periodic time-shuffling clutter filter angle sweep plan for L=4 segments and M=8 tilt angle firings per segment, with the y-axis representing the segment number, pattern-coded squares representing the tilt angles, and the numbers overlaid on pattern-coded squares representing the pulse number, demonstrating (a) time ordered sequence, and (b) angle ordered sequence; only 8 patterns are used, each representing a different value m.
Figure 10:
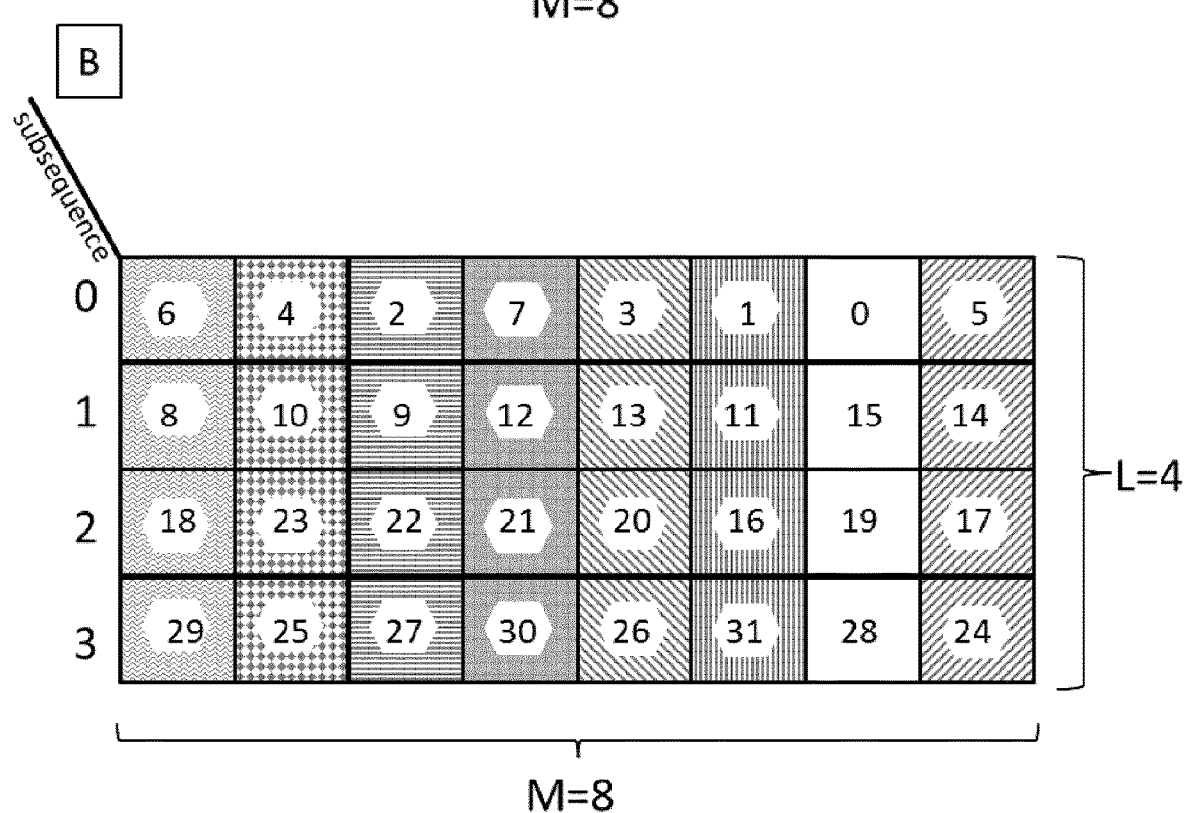

Mathematical Analysis: Additional Clutter Filtering—Periodic Time-Shuffling Clutter Filter (PTCF). For PTCF, the random angle sequence P(n) is further defined, of length N, as a concatenation of L unique uniformly distributed random subsequences or segments, each of length M and spanning the range [−M/2,M/2−1]. Note that throughout this section, P(n) denotes the pseudo-random sequence instead of PN(n) as used above, for example in Eq (18). FIG. 10 demonstrates this concept for the case of L=4 and M=8 and displays the time sequence n overlaid on top of the angle sequence P(n), where the tilt angles are represented by pattern-coded squares. Note that the figure shows the time sequence as spanning the range [0,N−1]instead of [−N/2,N/2−1] for ease of viewing. FIG. 10 shows that each pattern, representing a different tilt angle, is repeated only once per segment, and if the time sequence is unfolded to be linear instead of two-dimensional, the unfolded larger sequence is still random, but with less number of unique tilt angles than the sequence length. This is in contrast to TCF in which P(n) was a single sequence of length N, with no repeating numbers, and spanning all entries in the range [−N/2,N/2].

One possible implementation is using a linear feedback shift register (LFSR) of length M to produce a segment of length (M−1), and then randomly placing the '0' entry. By using different taps and starting phase, L different random segments can be produced, each is unique, uniformly distributed, and has non-repeating numbers, and the larger sequence is also random, uniformly distributed, but with each of the numbers repeating L times.

The transmit beam formation for PTCF uses N/L unique tilt angles instead of N, but this should not affect the beam resolution and sidelobes as long as N/L exceeds or is close to the limit described in Montaldo et al., ("Coherent Plane-Wave Compounding for Very High Frame Rate Ultrasonography and Transient Elastography," IEEE TUFFC, vol. 56, no. 3, pp. 489-506, 2009), which is typically between 60 and 70 tilt angles. Spread-spectrum suppression is expected to remain as $\sqrt{N}$ since that is the total length of the random sequence.

An advantage of this arrangement is that it allows for the retrospective selection of the Doppler ensemble's length so that it may assume any value from the set {M, 2M, 3M, ... ML}, since each would still be a random sequence. Another advantage is that since each tilt angle repeats L times, it is possible to view each sequence of similar tilt angles as a unique channel, on which conventional clutter filter may operate.

A derivation of PTCF can be achieved by analysis in the frequency domain (frequency domain formulation). P(n) is a mapping from time index n spanning N values to angle index m spanning M values as shown in FIG. 10A, i.e. m=P(n). Also, since P(n) is a many-to-one mapping (M<N), then a different inverse function $P_l^{-1}(m)$ exists for each segment, and it defines a mapping from angle index m to time index n within each segment l. If we wish to rearrange the signal in Eq. (18) such that it is angle ordered, then we need to perform index substitution, i.e. we need to compute $$LRI_{x_\beta z_\beta}(m=lM=M/2)=C(P_l^{-1}(m))e^{-jkPRIv_z P_l^{-1}(m)}$$
$$e^{-jkx_0 \delta m} e^{-jkPRIv_x \delta m P_l^{-1}(m)} \quad (22)$$

where m spans the range [−M/2,M/2−1] and l spans [−L/2,L/2−1]. FIG. 10B shows the angle ordered sequence, and demonstrates how the color-coded angles follow a sequential order while the associated (overlaid) time sequence is shuffled and is random since $P_l^{-1}(m)$ is also a random sequence. Note that the dependent parameters of the functions LRI ( ) and C( ) have been eliminated.

For a stationary clutter scatterer located at $(x_c, z_c)$, whether wall or tissue, its contribution is obtained by substituting $v_x = v_z = 0$ in Eq. (22), hence $$LRI_{c, x_\beta x_f}(m+lM+M/2)=C(x_c, z_c)e^{-jkx_0 \delta m} \quad (23)$$

which is a complex sinusoidal function of m, and $C(x_c, z_c)$ is constant for stationary scatterers. Additionally, irrelevant to frequency of the complex sinusoid, the signal in Eq. (23) is periodic with period M since l is not a variable inside the exponential. In other words Eq. (23) can be written in the form $LRI_{c, x_\beta x_f}(\text{index})=LRI_{c, x_\beta x_f}(\text{index}+M)$. Furthermore, since the signal in Eq. (23) has an ensemble length N that is an integer multiple of M, i.e. N=ML, then the FFT of Eq. (23) has coefficients that occur only at bins that are multiples of N/M=L.

The signal from a moving blood scatterer shall have a nonzero axial velocity however, and hence according to Eq. (22), its spectrum will not be periodic and will be spread. So, in essence the reshuffling causes the blood echoes to spread and the stationary clutter echoes to compact or de-spread and only occupy certain bins in the FFT.

Zeroing every $L^{th}$ bin in the FFT of the reordered signal removes the stationary part of the signal in Eq. (22) which represents stationary clutter (wall or tissue), but keeps non-stationary components which are not periodic and represent blood echoes.

An alternative derivation for the PTCF may be obtained by performing the analysis in the time domain (time domain formulation); if we rearrange the signal to the form in Eq. (22), and examine its representation in FIG. 10B, it is easy to imagine multiple mean filters, each operating on a unique tilt angle, i.e. each operating on one column with unique color shade. Stationary clutter may then be estimated as the mean value, and subtracted from the signal. Alternatively, we can run a single mean filter whose impulse response may be written as;

$$h(i) = \frac{1}{L}\sum_{l=0}^{L-1} \delta(i - lM) \qquad (24)$$

where h(i) is the impulse response and i is the sample index. If this filter is applied to the signal in Eq. (23) using circular convolution, then it effectively computes the average for each tilt angle (or pattern in FIG. 10B). This impulse response represents a pulse train with period M, and hence its FFT will also be a pulse train with period N/M=L. Subtracting the signal in Eq. (23) from the mean can be achieved by circular convolution with:

$$h(i) = \delta(i) - \frac{1}{L}\sum_{l=0}^{L-1} \delta(i - lM) \qquad (25)$$

which has zero-valued FFT bins at multiples of L. Hence zeroing the reordered signal's FFT bins at multiples of L is effectively filtering it with the impulse response of Eq. (25), which may be viewed as a multi-tap comb filter. Furthermore, this filter may be implemented in the time domain without the need of reordering by averaging samples of similar tilt angles and using that as the estimate of DC clutter and subtracting it from the corresponding sample, however, the FFT zeroing implementation may be more computationally efficient than circular convolution for large ensembles.

In experimental testing the spread-spectrum method is compared to conventional plane-wave color-Doppler in flow-phantom experiments. The results demonstrate the ability of the spread-spectrum method to accurately image high velocities (up to 400 mm/s) with better vessel delineation and contrast resolution than conventional plane-wave Doppler imaging. The following experimental examples are for illustration purposes only and are not intended to be a limiting description.

Flow-Phantom Experiment Method. Experiments were performed using a custom carotid artery flow phantom (Poepping et al., "A thin-walled carotid vessel phantom for Doppler ultrasound flow studies," *Ultrasound in Medicine and Biology*, vol. 30, pp. 1067-1078, 2004). The common carotid segment, which was imaged in this study, consisted of an 8-mm inner diameter and a 1-mm thick polydimethylsiloxane (PDMS) vessel surrounded by tissue-mimicking material (TMM) (Ramnarine et al., "Validation of a new blood-mimicking fluid for use in Doppler flow test objects," *Ultrasound in Medicine and Biology*, vol. 24, pp. 451-459, 1998). Constant 10 ml/s flow of the blood-mimicking fluid, prepared in house, was controlled using a Compuflow1000 precision pump (Shelley Medical Imaging Technologies, London, ON). A Sonix RP scanner (Ultrasonix Inc., Richmond, BC), equipped with a Sonix DAQ data acquisition module and a 60-mm, 128-element linear-array transducer (L14-5W/60), was used to acquire pre-beamformed channel data, sampled at 40 MHz with 12-bit quantization. A longitudinal view of the phantom's common carotid artery was imaged using a 5 MHz center frequency, 2-cycle transmit pulse, and a 15 kHz PRF. The transducer was oriented so the long axis of the vessel formed an 18° angle with the lateral dimension of the image. Post processing was performed using MATLAB (version R2015b, The MathWorks, Inc., Natick, Mass.). Color Doppler images were constructed using a lag-one autocorrelation method (Kasai et al., "Real-time two-dimensional blood flow imaging using an autocorrelation technique," *IEEE Transactions on Sonics and Ultrasonics*, Vols. SU-32, no. 3, pp. 458-464, 1985) for velocity estimation.

TABLE I

Sweep Plans Compared in the Flow-Phantom Experiment.

| | Sweep name | | |
| --- | --- | --- | --- |
| | LIN5 | LIN17 | RAND512 |
| Sweep type | Linear | Linear | Random |
| Number of angles in sweep (N) | 5 | 17 | 512 |
| Doppler ensemble length (M) | 100 (100 sweeps) | 32 (32 sweeps) | 512 (1 sweep) |
| Total number of frames | 500 | 544 | 512 |
| Tilt angle range $\alpha_{min}$: $\alpha_{max}$ (degrees) | −8.192 to 8.192 | | |
| Tilt angle step (δ) (degrees) | 4.096 | 1.024 | 0.032 |

Table I shows the three different sweep plans used in the experiments. The random angle sweep that implements the spread spectrum was compared against two linear sweep plans. All plans have approximately the same number of frames. Note that the RAND512 plan uses a single sweep and the length of the Doppler ensemble is equal to the length of the sweep since there is no compounding involved, whereas in the linear plans, the total number of frames is equal to the Doppler ensemble size (M) multiplied by the number of compounded angles (N).

Figure 7:
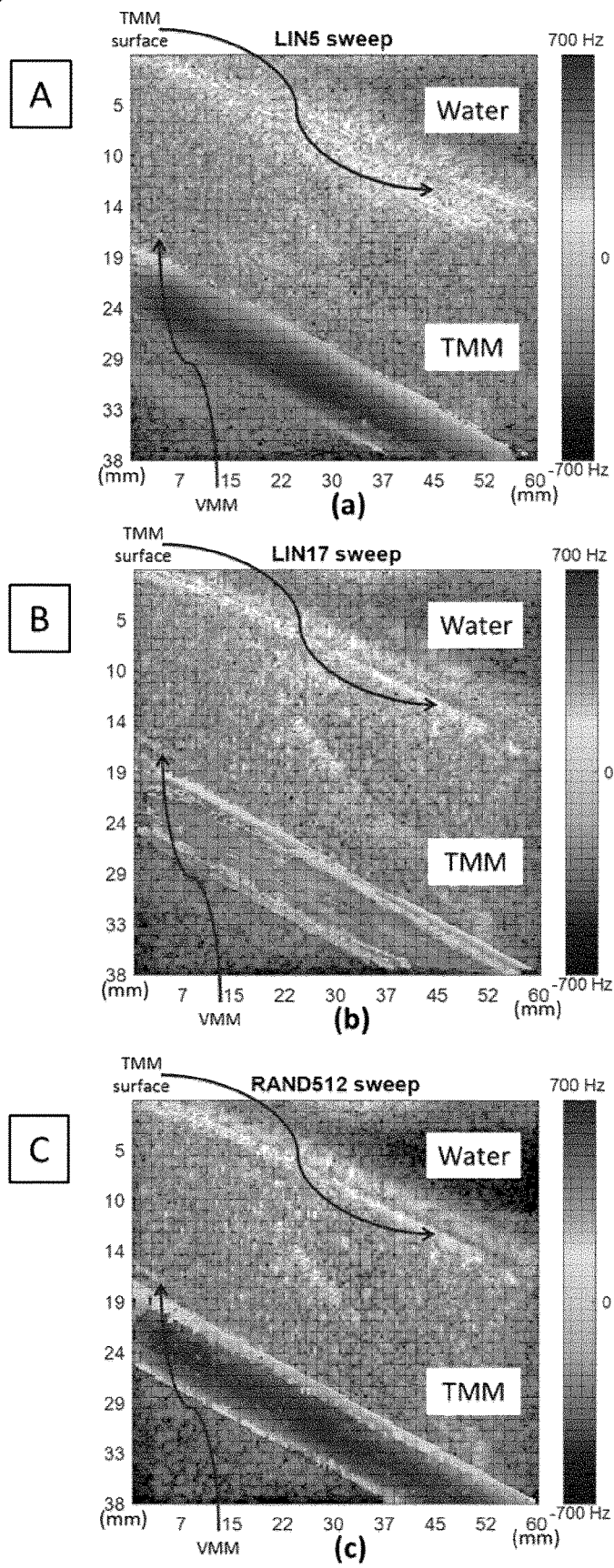
FIG. 7 shows Color Doppler images ((a), (b), (c)) and corresponding gray-scale representation ((d), (e), (f)) and B-mode images ((g), (h), (i)) of a thin-walled vessel phantom for the 3 sweep plans defined in Table I—LIN5 ((a), (d), (g)), LIN17 ((b), (e), (h), and RAND512 ((c), (f), (i)) with images spatially and temporally processed to improve clarity and gray-scale in (a), (b) and (c) displayed using a 50 dB dynamic range; (VMM=vessel mimicking-material; TMM=tissue mimicking material).
Figure 7:
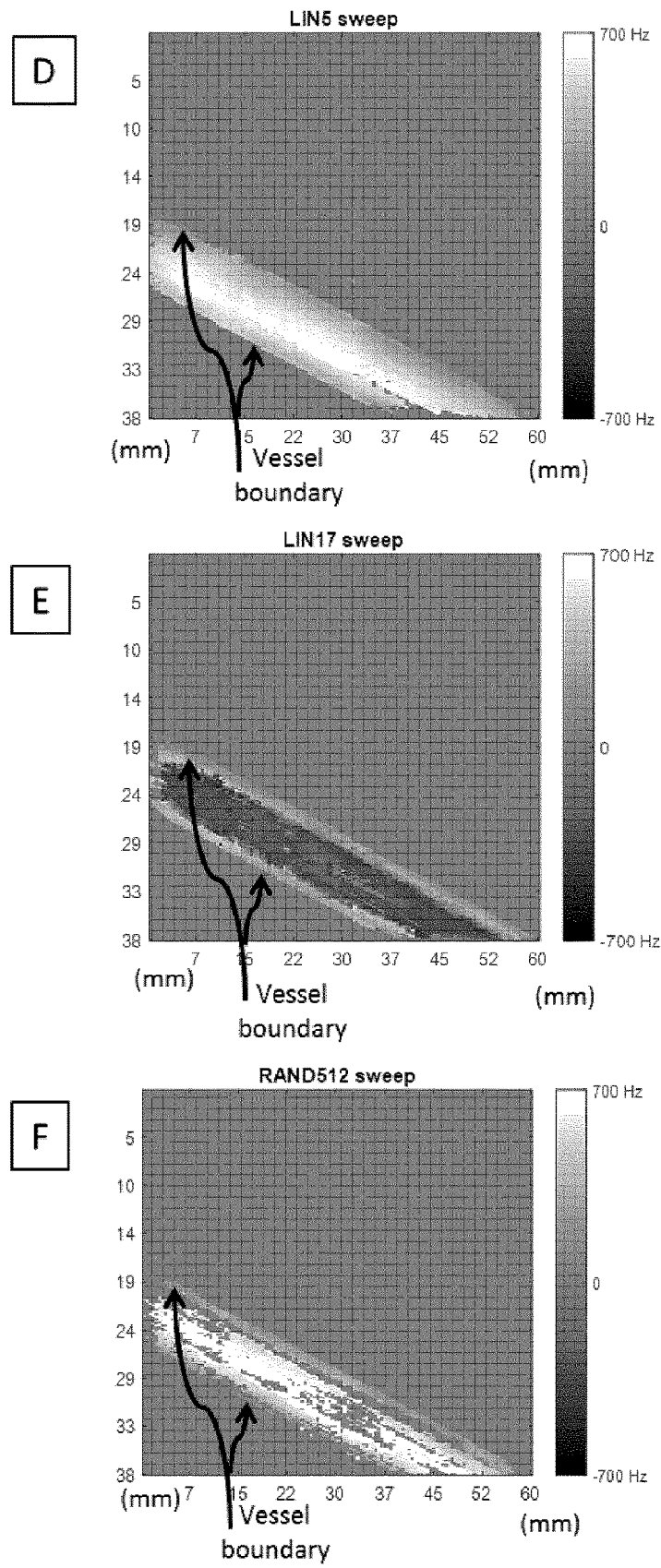
Figure 7:
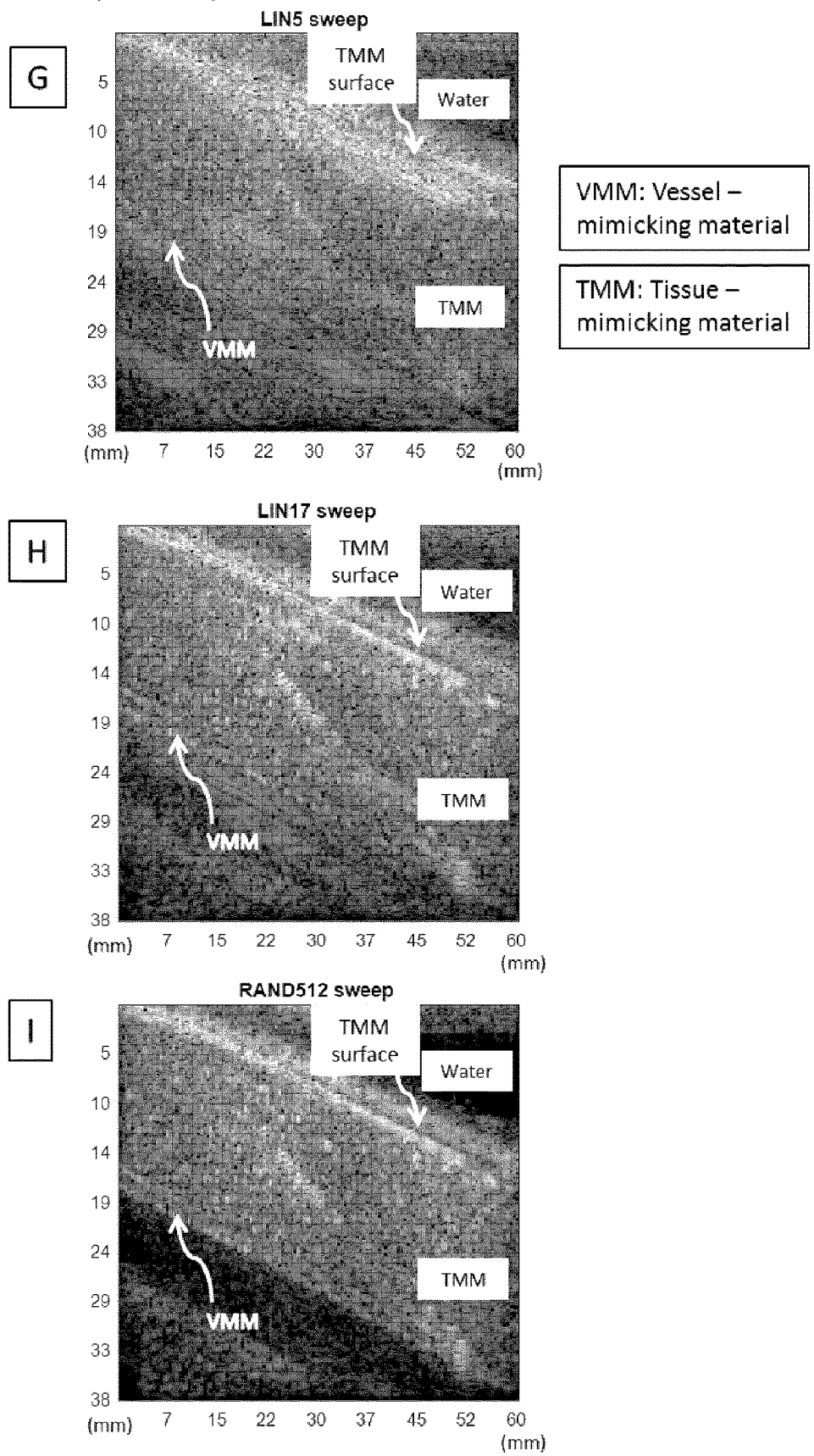

Flow-Phantom Experiment Results. In color Doppler imaging, pixels holding non-zero velocity information are overlaid over B-mode images. Each pixel's velocity estimate is quantized and converted into a color shade, with positive velocities represented in shades of red and negative velocities in shades of blue. Power Doppler images are formed in the same manner as in color Doppler flow, except that each pixel's power is computed and displayed instead of mean velocity estimates. FIG. 7 (A to C) shows color Doppler high-resolution images and corresponding full B-mode images (G to I) produced using the three different sweep plans. FIG. 7 (D to F) are gray-scale representations of 7A to 7C, respectively, showing the vessel isolated from the TMM background, with positive velocities represented in lighter shades (white) and negative velocities in darker shades (black). For the linear sweep plans, a color pixel is displayed if the power of the slow-time wall-filtered signal is above the $90^{th}$ percentile, whereas for the random sweep plan, a color pixel is displayed when the SNR is above the $90^{th}$ percentile. The different processing of the random-sweep images was necessary as a side effect of spreading the clutter over the entire bandwidth, which resulted in different background levels inside and outside the vessel. In the LIN5 image (FIGS. 7A and 7D), the color pixels extend outside the lumen more than in the other images. Velocity aliasing and suppression of higher velocities is evident in the LIN17 image (FIGS. 7B and 7E), with some areas near the center of the lumen showing no flow at all.

Figure 8:
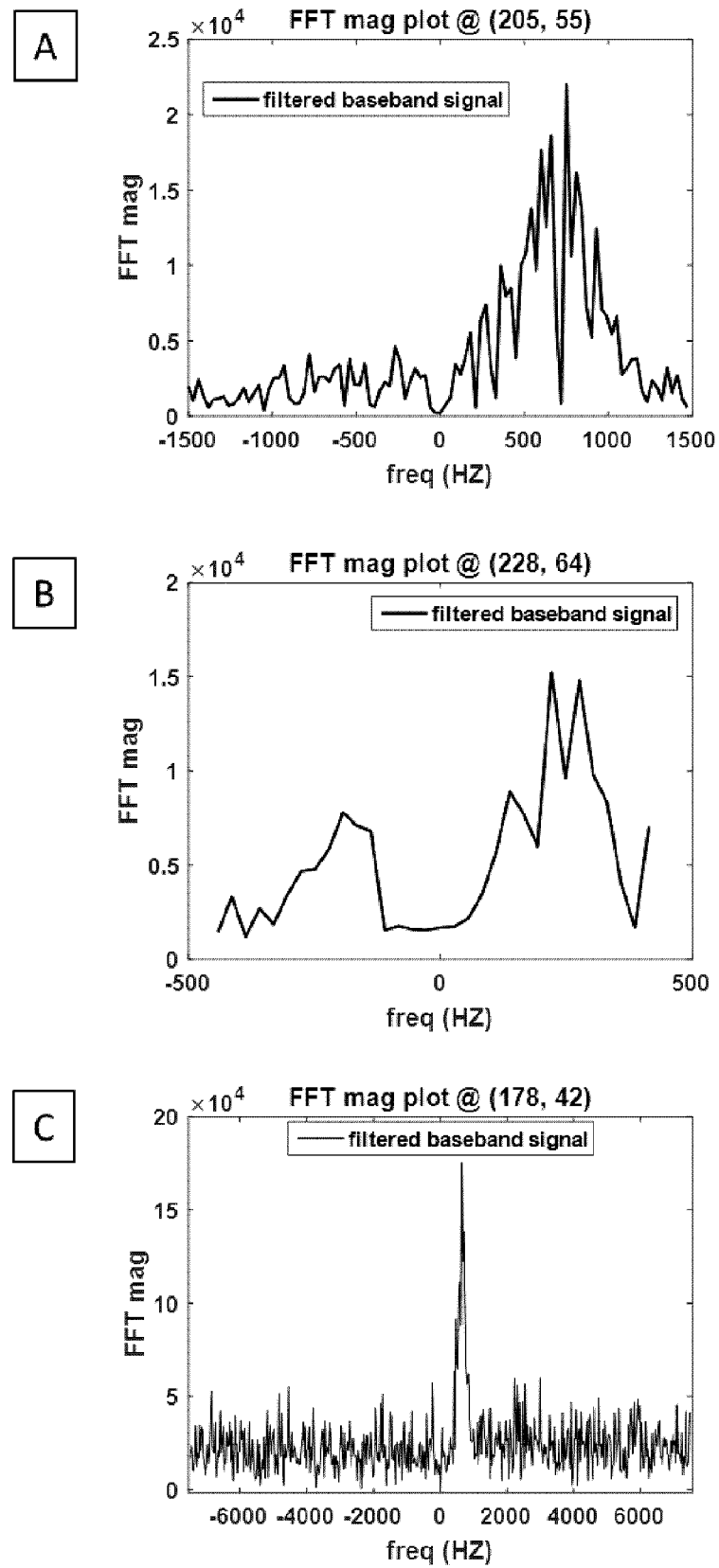
FIG. 8 shows Doppler spectra showing the FFT magnitude for a Doppler ensemble for each of the 3 sweep plans defined in Table I, demonstrating the effective slow-time sampling frequencies, 3 kHz, 0.882 kHz, and 15 kHz, respectively for the (a) LIN5, (b) LIN17, and (c) RAND512 sweep plans; data were acquired from the flow phantom shown in FIG. 7.

FIG. 8 shows the FFT of the slow-time signals from a representative color pixel for each of the three different sweep plans. Note that the sampling frequencies for the slow-time signals are 3 kHz, 882 Hz, and 15 kHz for the LIN5, LIN17, and RAND512 sweeps, respectively. In LIN5 and RAND512, the selected signal was that of a pixel near the center of the vessel, but it was near the bottom of the vessel for the LIN17 pixel to avoid pixels that produced aliased velocity estimates.

Figure 9:
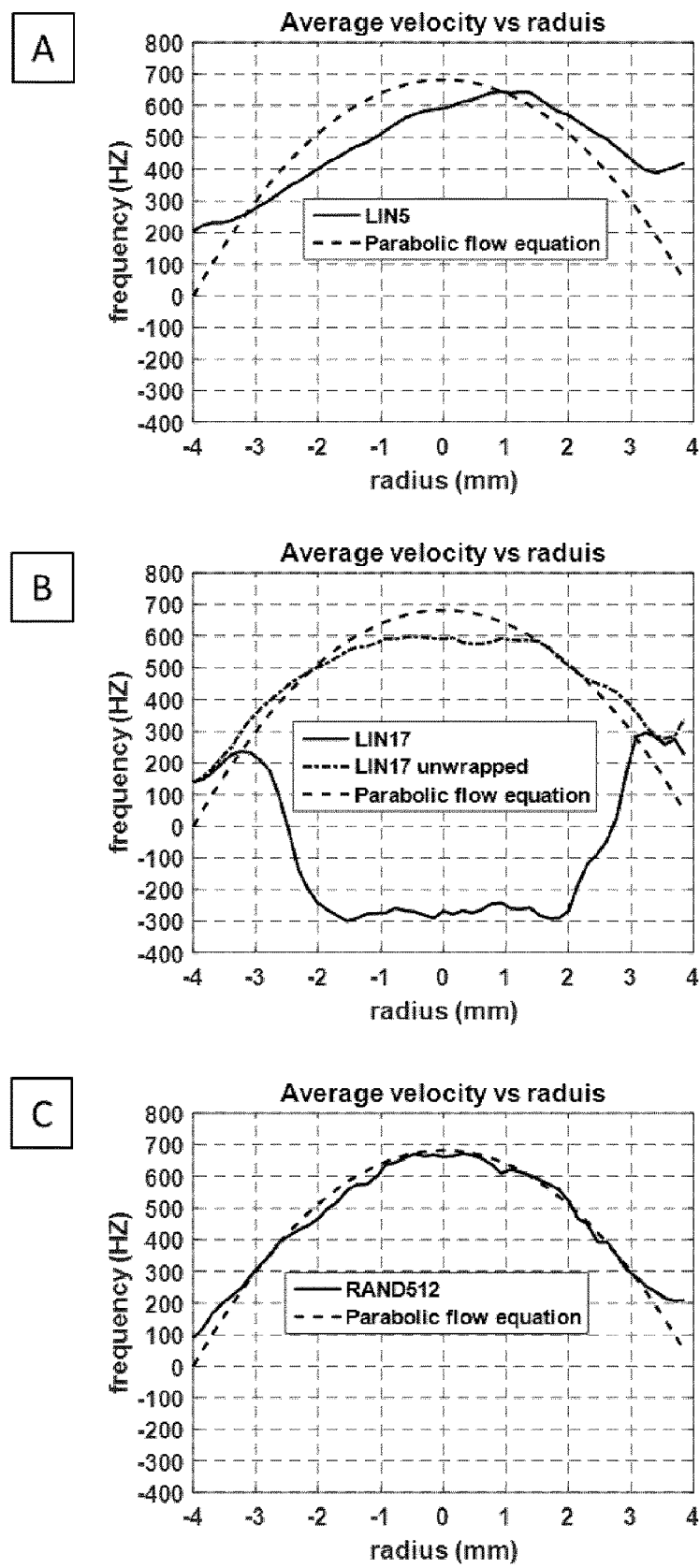
FIG. 9 shows measured average velocity profiles (as Doppler frequency shift) across the diameter of the flow phantom vessel using the three sweep plans defined in Table I (a) LIN5, (b) LIN17, and (c) RAND512—with the LIN17 profile in (b) shown before and after unwrapping aliased Doppler frequencies.

For each of the sweep types, mean frequencies were computed as a function of radius, r, by averaging pixels from the same radius along the length of the vessel for eight independent Doppler ensembles. FIG. 9 shows the mean velocity estimates for each sweep plan overlaid against a calculated ideal parabolic flow profile, $$v(r) = v_0\left[1 - \left(\frac{r}{r_o}\right)^2\right],$$

where $r_0$ is the vessel radius (4.3 mm when distended), r is the radial position of the velocity estimate within the vessel, and $v_0$ is the axial velocity at the center of the vessel (105 mm/s, computed based on 10 ml/s flow and an 18° vessel inclination angle). The velocity profile estimated using the LIN5 images (FIG. 9A) is flatter and also shifted to the right compared to the ideal profile. This may be attributed to the elevated side-lobes in the LIN5's beam pattern, which produced equal but elevated contributions from scatterers on either side of the focal point. In this image, scatterers on the right side contribute more signal power due to lower attenuation since their echoes travel through more transducer coupling fluid (water) and less blood-mimicking fluid, thereby skewing the velocity profile. In the LIN17 velocity profile (FIG. 9B), due to aliasing, negative velocities were estimated, and even after velocity unwrapping by adding the slow-time sampling frequency (PRF/N=882 Hz) to any negative frequency, the profile plateaus prior to reaching the maximum velocity of 105 mm/s, which corresponds to a Doppler frequency of 700 Hz. In contrast, the RAND512 velocity profile (FIG. 9C) is closest to the ideal parabolic flow profile.

The above mathematical analysis, which was confirmed by a wire target experiment, demonstrates that off-focus strong scatterers, such as the vessel wall, produce echoes whose phase is a function of the incident plane-wave direction. If the transmit angle is varied in a linear sequence and if compounding is not performed, an off-focus strong scatterer produces a narrowband tone in the resulting Doppler spectrum (FIG. 4). Therefore, compounding, which is ordinarily viewed as a method to improve image contrast and resolution in the spatial domain, can equivalently be viewed as a method to suppress those narrowband tones in the Doppler frequency domain. The spread-spectrum method instead suppresses the Doppler signal from an off-focus scatterer by randomizing its phase, thereby removing a need for compounding. The spread-spectrum method thus incorporates an initial clutter-filtering operation into a beamforming procedure for high-frame-rate imaging.

The spread-spectrum method is designed to circumvent the trade-off between beam quality, particularly side-lobe and grating-lobe levels, and maximum unaliased Doppler frequency that is present in current Doppler imaging methods. The flow-phantom experiment was intended to illustrate this capability by comparing the spread-spectrum method to an implementation of a compounding-based method that emphasizes beam quality at the expense of maximum Doppler frequency (LIN17) and a second approach (LIN5) that makes the opposite compromise. The numbers of sweep angles used in the two linear-sweep plans are representative of typical implementations of plane-wave color Doppler. Aliasing of Doppler frequencies >441 Hz is visually apparent in the LIN17 image (FIG. 7B). The corresponding estimated velocity profile (FIG. 9B) highlights the consequences of LIN17's relatively low slow-time sampling rate because it was not possible to correct the Doppler estimates near the center of the vessel by unwrapping the aliased frequencies.

The differences in beam quality among the three transmit sweep plans is also easily recognized by observing the difference in contrast resolution in the B-mode image data (FIG. 7) between the tissue-mimicking material (TMM) and the water used for acoustic coupling. The spread-spectrum image (FIGS. 7C and 7I) is noticeably superior in this regard to the images produced using the two linear sweep plans (FIGS. 7A, 7G and 7B, 7H). Close inspection of the linear-sweep images also reveals subtle blooming artifacts just outside the vessel wall in the phantom, whereas the vessel boundary is more sharply delineated in the spread-spectrum color Doppler image, which indicates that the spread-spectrum method also provides higher spatial resolution.

Field II Simulation—TCF and PTCF—Experiment Setup. Synthetic images were produced using Field II (J. Jensen, "FIeld: A program for simulating Ultrasound systems," Medical and Biological Engineering and Computing, vol. 34, pp. 351-353, 1996) simulations running on MATLAB software (version R2016b, The MathWorks, Inc., Natick, Mass.) with the parallel processing toolbox, and with the parameters shown in Table II. The Scatterers were placed randomly throughout the imaging scene, and then three different scatterer populations were formed for blood, tissue, and wall echoes according to the relative magnitudes in Table II. At each time step equal to 1/FR, where FR is the frame rate, blood scatterers were allowed to move with constant velocity using a parabolic flow profile in the form $v=V_0[1-(r/R)^2]$, where $V_0$ is the maximum frequency, r is the scatterer's radial position within the vessel, and R is the vessel's inner radius. At every time step, the Field II program is run using plane-wave excitation with tilt angles obtained from a predetermined sweep plan as shown in Table III. The random angle sweeps (RAND512 and RAND64×8) implement a random sequence of plane-wave angles and use spread-spectrum beamforming, while the LIN1 plan implements a single plane-wave tilt angle and hence does not implement retrospective transmit beamforming. Frame compounding is not performed in any of the sweep plans. The LIN1 plan was selected since it does not require any compounding, and hence does not reduce the frame rate thereby allowing a comparison of its Doppler spectrum to those of the other two random sweep plans. This comparison includes measuring the Doppler peak and noise levels without aliasing concerns.

Receive beamforming was applied to RF data acquired by the field simulations, and the resulting beamformed RF image frames were quadrature demodulated to produce I/Q samples that form Doppler ensembles of length 512, corresponding to 512 acquired frames. Three simulations were run for the different sweep plans of Table III. For clutter rejection, the LIN1 plan used a 100 Hz high-pass finite impulse response (FIR) filter, the RAND512 plan used TCF, and finally the RAND64×8 plan used PTCF.

TABLE II

Field II setup parameters.

| | |
|---|---|
| Number of Scatterers per resolution cell | 20 |
| Imaging scene (depth, width, thickness) in mm | 80, 60, 1 |
| Wall-to-blood ratio (linear) | 100 |
| Tissue-to-blood ratio (linear) | 40 |
| Vessel tilt angle (from horizontal) | 20° |
| Velocity profile | Parabolic |
| Maximum velocity $V_0$ | 400 mm/s |
| Vessel's inner diameter | 8 mm |
| Frame rate (FR) | 15 kHz |
| Excitation frequency | 5 MHz |
| Number of cycles per pulse | 2 |
| Tilt angle sweep plan | LIN1, RAND512, an RAND64x8 |
| Total number of firings | 512 |
| Transducer type | Linear array |
| Number of elements | 128 |
| Element Pitch | 0.472 mm |
| Element kerf | 0.025 mm |
| Element height | 4 mm |

TABLE III

Sweep parameters

| | Sweep name | | |
|---|---|---|---|
| | LIN1 | RAND512 | RAND64x8 |
| Sweep type | Linear | Random | Random |
| Number of unique tilt angles in sweep (M) | 1 | 512 | 64 |
| Doppler ensemble length (N) | 512 | 512 | 512 |
| Tilt angle range $\alpha_{min}:\alpha_{max}$ (degrees) | 0 | −8.192° to 8.192° | −8.192° to 8.192° |
| Tilt angle step ($\delta$) (degrees) | 0 | 0.032° | 0.256° |

A pixel is deemed to be a color pixel if its frequency lies between 50 and 1500 Hz, its Doppler signal's peak-to-noise ratio (PNR) exceeds the $80^{th}$ percentile PNR of all pixels within the image, and its b-mode level is below the $50^{th}$ percentile. The PNR is defined as the ratio of peak FFT magnitude of the Doppler slow time signal to its median magnitude.

Field II Simulation Results.

Color and PNR images (not shown) were produced for the field simulated vessel. The vessel fill ratio is evident in the color images, where it is almost full for all three sweep plans. The PNR images demonstrate a 14 dB PNR advantage of the RAND64×8 plan over the RAND512. Since field simulations were run without injecting noise into the RF data, the noise-like disturbance in the signal's spectrum is solely due to clutter that is spectrally spread due to the randomized angle sweep plan and made to look noise-like and hence the difference in PNR is solely due to the improved clutter suppression in the segmented sweep.

By examining PNR images and the associated color bar for the RAND64×8 sweep, we can estimate the PNR to lie mostly between 24-32 dB level, with the average value of 26 as shown in Table IV. If a single blood scatterer exists outside a particular resolution cell, i.e. representing beamforming clutter, then theoretically the spread-spectrum suppression of that single scatterer due to 512 random tilt angles is $20 \log_{10}(\sqrt{512})=27$ dB suppression. Since the blood vessel contains many scatterers, we can roughly approximate their combined energy outside the mainlobe of the receive beamformer to be the same as that inside the mainlobe (in-cell scatterers), then PNR values of 24-32 dB seem like a reasonable number to expect. PNR images for the RAND512 sweep display lower levels of PNR indicating inferior stationary clutter suppression (wall or tissue) of TCF compared to PTCF. In the LIN1 sweep, the PNR levels are not applicable since there is no clutter spreading and with lack of noise in the RF data, the median of the Doppler signal's FFT then only represents windowing sidelobes which are very low.

FIG. 11H demonstrates this point by showing the wall filtered version of the Doppler signal of FIG. 11A measured at a typical pixel ($184^{th}$ point of scanline 58). FIG. 11B and FIG. 11C show the FFT of the slow time Doppler signals for the RAND512 and RAND64×8 sweeps respectively at the same location, and demonstrate the lack of any discernible signal in either one of them prior to clutter filtering. The next row (11D and 11E) shows the FFT of the angle-ordered signals, demonstrating the existence of distinct spectral lines occurring every 8th bin in the RAND64×8 sweep plan (FIG. 11E) representing stationary clutter as described in Eq. (23), and lack of such lines in the RAND512 sweep (FIG. 11D) since its clutter signal is not periodic. Additionally, it may be observed that FIG. 11D and FIG. 11E both exhibit two spectral peaks that represent the vessel walls (verified by evaluating their frequency and translating it into lateral displacement from the measured pixel using Eq. (22)). Moreover, the peaks of the RAND64×8 plan occur at higher frequencies (≈4 kHz) than those in the RAND512 plan (≈500 Hz), i.e. 8 times slower, which may be explained by examining the frequency of the exponential in Eq. (22) and recalling that the angle step $\delta$ is 0.256° in the RAND64×8 but 0.032° in the RAND512 plan—in other words, the RAND64×8 sweep goes through the entire range of tilt angles 8 time faster that the RAND512, and hence clutter appears at higher frequencies.

Figure 11:
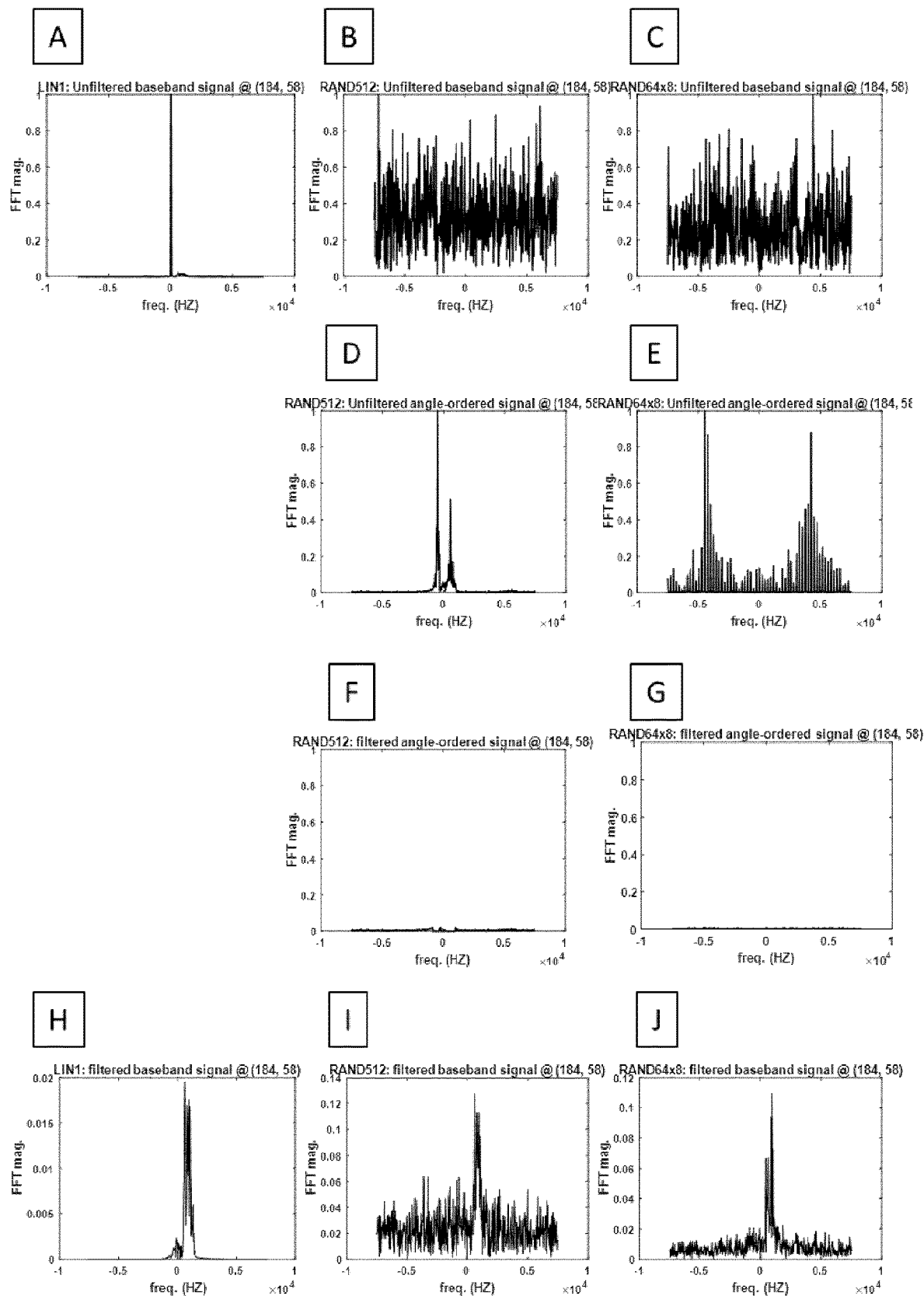
FIG. 11 shows FFT plots for Field II simulations FFT of slow time (Doppler) signals demonstrating the clutter filtering chain for three different sweep plans summarized in Table III.
Figure 12:
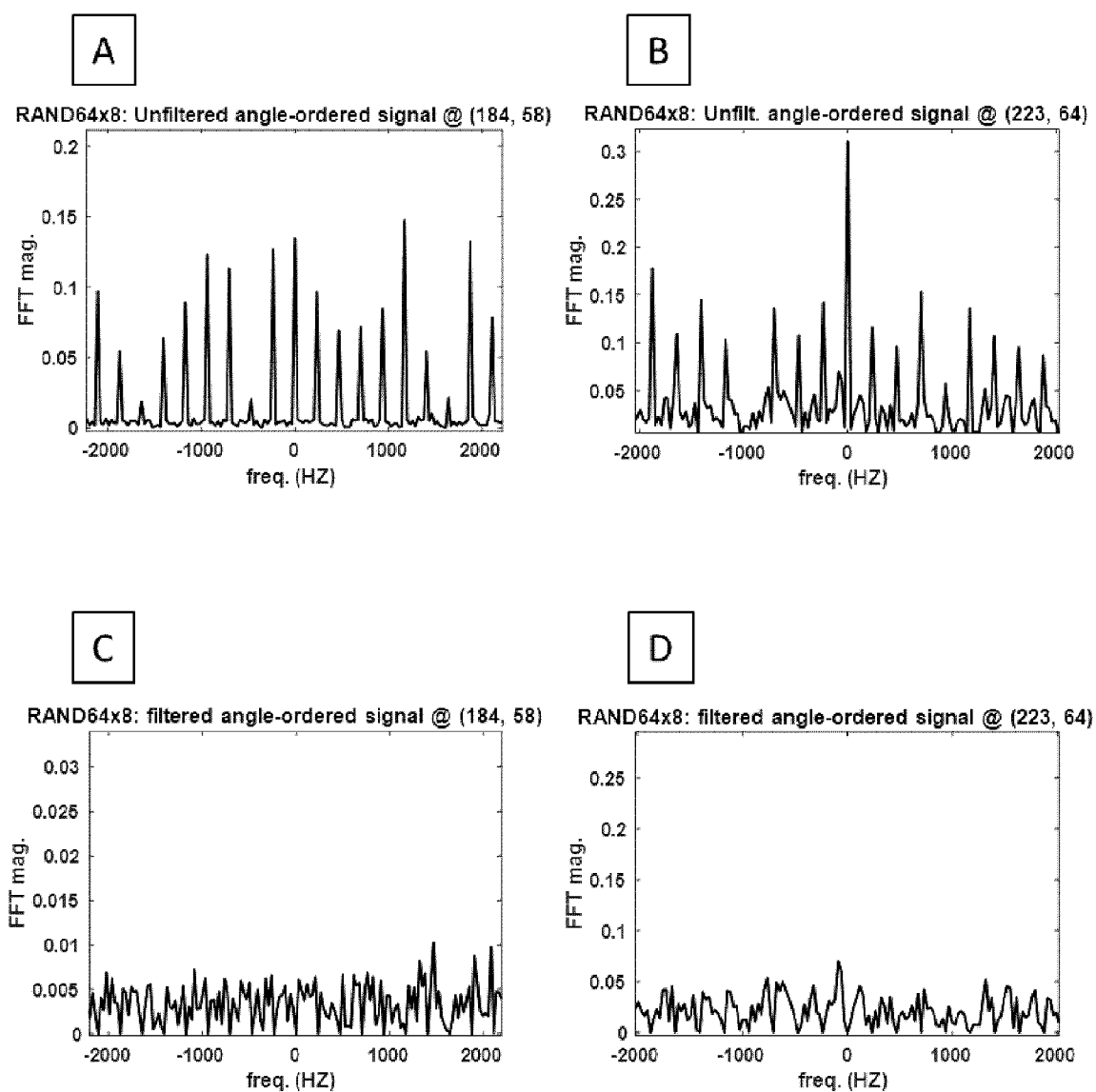
FIG. 12 shows zoomed in plots for the FFT of the angle ordered signals demonstrating the stationary clutter spectral lines and the operation of the periodic reshuffling comb filter; (A,C)—Field II simulations shown in FIG. 11; (B,D)—Flow phantom experiment shown in FIG. 13.

The next row of FIG. 11 (F and G) and its zoomed-in version in the left panel of FIG. 12 demonstrates the clutter filtering method. Whereas in the RAND512 using the TCF method, a threshold is manually calibrated as 0.1 of the peak FFT magnitude and all bins with magnitudes above that threshold are cleared, the RAND64×8 using the PTCF method only clears FFT bins that are multiples of 8 without the need of any manually calibrated thresholds.

The bottom row of FIGS. 11(H, I and J) shows the FFT magnitude of the filtered time-ordered signals. The LIN1 exhibits the higher PNR, with the reasoning previously discussed, but it has the widest bandwidth, since out-of-cell clutter from blood scatterers is not attenuated as in the other two sweep plans. A comparison between FIGS. 11I and 11J demonstrates the improved clutter suppression in the PTCF method.

Flow Phantom Experiment—TCF and PTCF—Methods.

Experiments were performed using a custom carotid artery flow phantom. The common carotid segment, which was imaged in this study, consisted of an 8-mm inner diameter and a 1-mm thick polydimethylsiloxane vessel wall surrounded by tissue-mimicking material. Constant flow of blood-mimicking fluid, prepared in house, was controlled using a Compuflow1000 precision pump (Shelley Medical Imaging Technologies, London, ON). A Sonix RP scanner (Ultrasonix Inc., Richmond, BC), equipped with a Sonix DAQ data acquisition module and a 60-mm, 128-element linear-array transducer (L14-5W/60) was used to acquire pre-beamformed channel data sampled at 40 MHz with 12-bit quantization.

A longitudinal view of the phantom's common carotid artery was imaged using a 5 MHz center frequency, 2-cycle transmit pulse, and a 15 kHz PRF. Two different transducer orientations were tested; the high tilt orientation, where the transducer was oriented so the long axis of the vessel formed a 20.5° angle with the lateral dimension of the image, and the low tilt orientation with a 10° angle. Additionally, two constant flows were tested; 10 mL/s and 5 mL/s, for a total of four distinct experiments, and each experiment had 8 independent Doppler image frames.

Three different sweep plans (Table III) were used in the experiments and the same post processing steps used in the Field II simulations were also used with experimental data.

Flow Phantom Experiment Results.

Color and PNR images (not shown) of the flow phantom experiments demonstrate the improvement in vessel fill in the PTCF method (with RAND64×8 sweep) compared to the TCF method (with RAND512 sweep), and also an improvement in PNR as seen in higher percentage of red and yellow colors in the PNR image for PTCF compared to the PNR image for TCF. The vessel fill and the PNR ratios in the spread-spectrum sweeps are lower than that of the LIN1 sweep, which uses a traditional 100 Hz high-pass wall filter.

Figure 13:
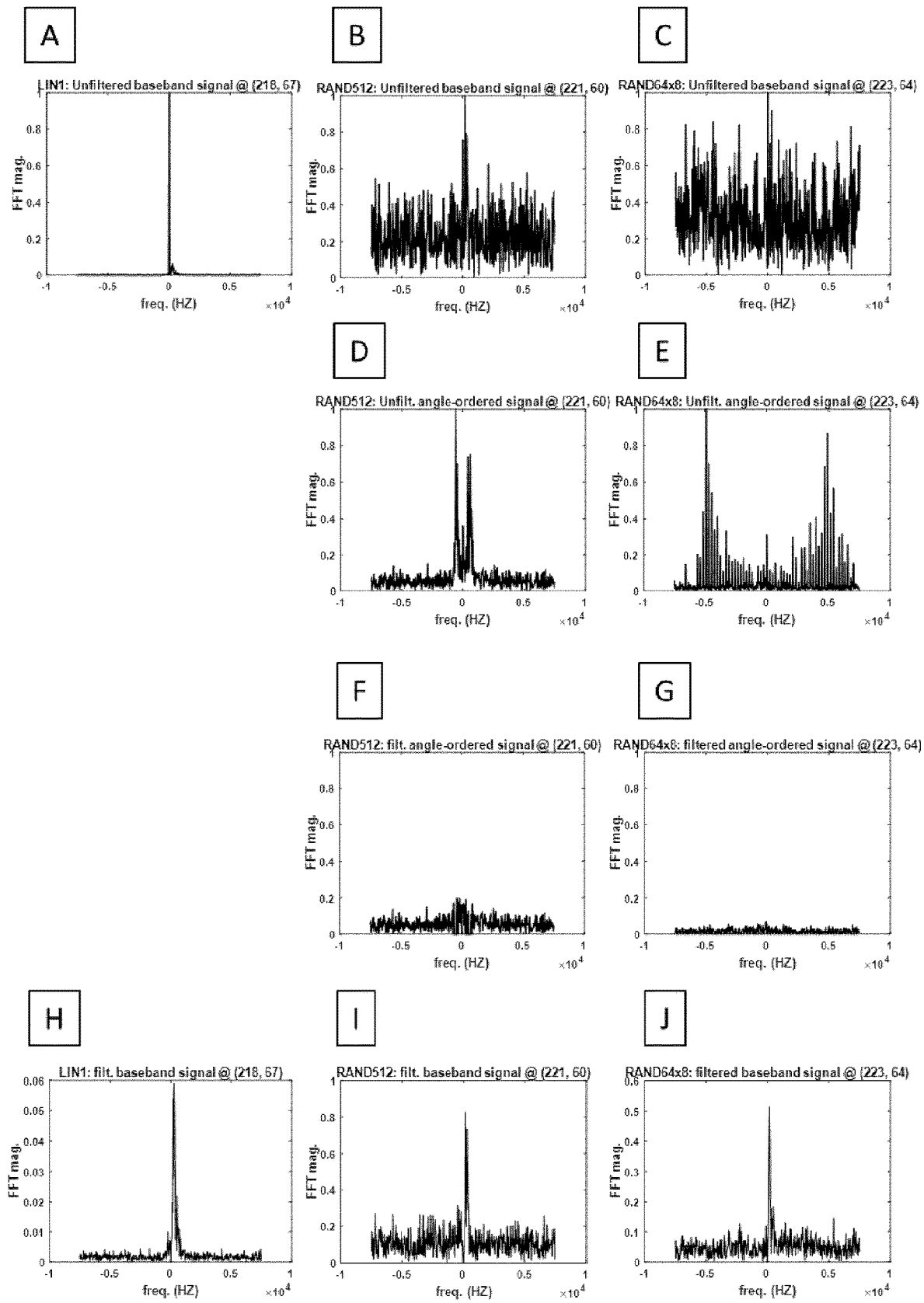
FIG. 13 shows FFT plots for flow phantom experiments—FFT of slow time (Doppler) signals demonstrating the clutter filtering chain for three different sweep plans (Table III).

FIG. 13 shows the FFT of typical Doppler signals going through the three different processing chains as in FIG. 11, except that a carotid flow phantom is used instead of simulation data. FIG. 13H demonstrates the LIN1 filtered Doppler FFT magnitude in the presence of noise, which is in contrast to FIG. 11H in which the Field simulated data did not model the noise, thus displaying unrealistically high PNR.

evaluating the PNR average measurements. The RAND64×8 using the PRCF method always outperformed the RAND512 with RCF by about 3-4 dB even though three of the four RAND64×8 experiments had lower signal peak levels. The average bandwidth in the two random sweeps is observed to be lower by a factor of 8-10 than that measured in the LIN1 sweep experiments, which is consistent with higher spatial resolutions in the random sweeps. The bandwidths differed in the field simulations only by a factor of 2 however, but we believe this may be due to using only a 1 mm image scene thickness.

TABLE V

TPF measurements for the three sweep plans using four different setups.

|  | TPF | | |
| --- | --- | --- | --- |
|  | LIN1 | RAND512 | RAND64×8 |
| Phantom Experiment: High tilt, 5 mL/s. | 0.9 | 0.13 | 0.69 |
| Phantom Experiment: High tilt, 10 mL/s. | 0.97 | 0.23 | 0.58 |
| Phantom Experiment: Low tilt, 5 mL/s. | 0.79 | 0.15 | 0.47 |
| Phantom Experiment: Low tilt, 10 mL/s. | 0.84 | 0.17 | 0.35 |

Calculations were performed to determine the true positive fraction (TPF), defined as the ratio of detected color pixels inside the vessel to the total number of pixels within the vessel. Table V shows measured TPF values for the three different plans, using four different setups; a high tilt carotid vessel phantom (angle between vessel axis and the horizontal line is 19.5°) with and 5 mL/s constant flows, and a low

TABLE IV

Doppler parameter averages for three sweep plans.

|  | Peak$_{av}$ (dB) | | | PNR$_{av}$ (dB) | | | Bandwidth ($\sigma_{av}$) (Hz) | | |
| --- | --- | --- | --- | --- | --- | --- | --- | --- | --- |
|  | LIN1 | RAND 512 | RAND 64 × 8 | LIN1 | RAND 512 | RAND 64 × 8 | LIN1 | RAND 512 | RAND 64 × 8 |
| Field II simulation: High tilt, 10 mL/s | 117 | 115 | 116 | 59 | 16 | 26 | 179 | 80 | 93 |
| Phantom Experiment: High tilt, 5 mL/s. | 93 | 94 | 87 | 31 | 14 | 18 | 988 | 32 | 49 |
| Phantom Experiment: High tilt, 10 mL/s. | 94 | 96 | 87 | 33 | 15 | 17 | 780 | 46 | 62 |
| Phantom Experiment: Low tilt, 5 mL/s. | 98 | 96 | 89 | 35 | 14 | 16 | 735 | 45 | 41 |
| Phantom Experiment: Low tilt, 10 mL/s. | 95 | 95 | 94 | 33 | 14 | 15 | 629 | 65 | 61 |

Table IV shows the peak, PNR, and bandwidth parameters averaged over an area of 9×9 pixels, centered at the intersection of scanline 60 and the vessel's center axis. For each sweep type, we computed average values for one Field II simulation with a single Doppler ensemble (512 frames) and four flow phantom experiments with two orientations (high and low) and two flow rates (5 mL/s and 10 mL/s).

The average peaks of the Doppler signals FFT magnitudes are presented so that they are taken into account when tilt (12.3°) carotid phantom setup using 10 and 5 mL/s constant flows. For each experiment, the values were averaged over 8 independent Doppler frames. Data shows that the PTCF method (RAND64×8, third column) outperformed the TCF method (RAND512, second column) in all experiments.

PTCF has been shown in the above simulations and flow phantom experiments to significantly improve wall and tissue clutter rejection as compared to TCF. Field II simulations showed excellent clutter rejection using PTCF. Flow phantom experiments showed improved performance over the TCF method.

An illustrative version and several variants of a spread-spectrum Doppler measurement method and system have been described above without any intended loss of generality. Further examples of modifications and variation are now provided. Still further variants, modifications and combinations thereof are contemplated and will be apparent to the person of skill in the art.

In the context of spread-spectrum Doppler described herein certain terms may be used interchangeably. For, example, color Doppler imaging and color Doppler flow imaging are used interchangeably. Power Doppler and power Doppler flow are used interchangeably. Steering angle and tilt angle are used interchangeably. Slow-time sampling rate and Doppler sampling rate are used interchangeably within the spread-spectrum Doppler described herein, but may not necessarily be used interchangeably in other Doppler techniques.

In spread-spectrum Doppler, echo data is the data acquired by the receive side of the transducer array and sampled by the system analog-to-digital converter. Transmit data may be used in processing the acquired echo data. Transmit data relates to information derived from any component of a transmit pulse as well as any parameter of the transmit pulse including, for example, the transmitted waveform, the waveform envelop (may be used for matched filtering prior to demodulation), the transmitted RF frequency (for frequency to velocity conversions, and possible Doppler shift estimation), or the pulse repetition interval (for computing the Doppler frequency shift) or the transmit tilt angle.

In spread-spectrum Doppler a visual representation of a target object is optionally provided. When a visual representation is displayed, a pixel corresponding to a Doppler parameter is displayed in the visual representation when the Doppler parameter has a signal-noise-ratio or a peak-noise-ratio above a predetermined threshold. The predetermined threshold is adjustable and can be any convenient threshold suited to a particular implementation. As an example, quite often the predetermined threshold will be greater than the $50^{th}$ percentile of all pixels within an image or a specified window or portion within an image. In other examples, the predetermined threshold may be greater than about the $60^{th}$ percentile, greater than about the $70^{th}$ percentile, greater than about the $80^{th}$ percentile or greater than about the $90^{th}$ percentile.

The spread-spectrum Doppler can be used to calculate or quantify any Doppler parameter including, for example, velocity, power, direction, bandwidth, or variance.

The spread-spectrum Doppler can typically accommodate transducers that are conventionally employed in plane-wave imaging or synthetic aperture imaging. Examples of suitable transducers include linear array transducers, phased array transducers, 2-dimensional matrix array transducers. Typically, the spread-spectrum Doppler will not accommodate annular arrays, and mechanically scanned single element transducers.

The spread-spectrum Doppler can accommodate many types of random generator including true random number generators that produce truly random sequences (https://en.wikipedia.org/wiki/Hardware_random_number_generator) as well as generators of pseudo-random sequences.

Receive beamforming can optionally be incorporated to benefit spread-spectrum Doppler. Conventional receive beamforming techniques may be used. Many receive beamforming techniques are recognized and may be incorporated as desired depending on a specific implementation.

Optional use of demodulation techniques may also benefit spread-spectrum Doppler. Demodulation techniques such as quadrature demodulation can readily be incorporated.

Traditional clutter filters such as finite impulse response (FIR) and infinite impulse response (IIR) cannot be directly applied in spread-spectrum Doppler. A characteristic of a filter that may be useful with the spread-spectrum method is a filter that includes reordering of at least a portion of the Doppler ensemble to be angle-ordered; TCF and PTCF are examples of useful filters.

PTCF may be extended to filter non-stationary clutter which will enhance its value for clinical applications of spread-spectrum Doppler by providing high spatial resolution of high velocities including, for example, blood flow in heart chambers, aortic arch, or stenosis and turbulence detection in the carotid and other large vessels.

For example, PTCF can be adapted to filter non-stationary clutter by pre-multiplying the time-ordered signal by $e^{j\omega_c t}$ where $\omega_c$ is the central frequency of the clutter and may be estimated by the following two step procedure: first, for multiple values of angular frequency $\omega$, multiply the time-ordered signal by $e^{j\omega t}$ angle-order the multiplied signal, apply the mean filter defined in Eq. (24), and compute the output signal's energy; and second, choose the value of $\omega$ with the maximum output energy.

While PTCF can be applied using any plurality (ie., two or more) of subsequences or sequence segments, often PTCF will be applied using four or more subsequences.

In PTCF an overall sequence of transmit pulses comprises a plurality of subsequences, each of the plurality of subsequences comprising a unique random ordering of a common set of the adjustable steering angles. Any number and degree of steering angles can be included in the common set as suited to a particular implementation of the spread-spectrum Doppler. Since the subsequences derive from a common set each subsequence will have the same set of steering angles as other subsequences, but the subsequences will differ in the ordering of the steering angles.

The spread-spectrum Doppler may be applied to measurement of motion of varied targets including both medical and non-medical applications. For medical applications, targets may include blood flow or tissue motion in a human or animal body part. A typical targeted body part with the blood flow or tissue motion is a heart chamber or its surrounding tissue, an aortic arch or its surrounding tissue, a carotid artery or its surrounding tissue, or any large blood vessel or its surrounding tissue.

The spread-spectrum Doppler is expected to be best suited for Doppler imaging in areas with high velocity, such as heart chambers, aortic arch, carotid artery, and other large vessels. High impact can be anticipated when imaging areas where the Doppler angle spans a large range, such as the aortic arch, or in cases of stenosis and turbulent flow. In such cases, aliasing is more likely to occur due to the increased likelihood of flow being parallel to the transducer axis, thereby resulting in higher Doppler shifts. In addition, the method may be adapted to suit other applications, such as synthetic aperture and elasticity imaging. This technology may be of particular interest for three-dimensional (3-D) Doppler imaging using synthetic aperture due to its potential to reduce the number of transmissions per frame, which is ordinarily squared when moving from 2-D to 3-D imaging.

The spread-spectrum Doppler can be adapted to any number of currently recognized modes of Doppler imaging (Shung, Diagnostic Ultrasound, Boca Raton, Fla.: CRC press—Taylor & Francis Group, 2006; Jensen et al., "Synthetic aperture ultrasound imaging," Ultrasonics, vol. 44, pp. e5-e15, 2006) including, for example, vector Doppler imaging, color flow Doppler imaging, power flow Doppler imaging, spectral Doppler imaging, plane-wave imaging, 3D Doppler imaging, elasticity imaging, synthetic aperture imaging, blood Doppler imaging or tissue Doppler imaging.

In conventional synthetic-aperture imaging (also known as synthetic transmit aperture imaging), spherical ultrasound pulsed waves are transmitted from a single transducer array element, illuminating the entire imaging scene, and the corresponding low resolution image (LRI) frame is produced by acquiring RF samples from all the transducer's receive elements simultaneously. Alternatively, in order to increase the transmitted power, multiple adjacent transducer array elements are fired simultaneously after applying the appropriate transmit delays to synthesize a de-focused or a spherical beam, thus emulating the single transducer array element and creating a virtual source, and similarly the corresponding LRI frame is acquired. The process is repeated multiple times, sequencing through the transducer array elements or virtual sources from right-to-left or left-to-right linearly along the transducer array. Similar to conventional plane-wave imaging, multiple (N) LRI frames are coherently summed to produce a single HRI frame, thus reducing the HRI frame-rate to PRF/N and M HIM frames are used to construct the Doppler ensemble, and hence the compromise between spatial resolution and the maximum unaliased Doppler frequency shift exists as in conventional compounded plane-wave imaging.

As opposed to sequencing through the transducer array elements or virtual sources from left-to-right or right-to-left in conventional synthetic-aperture imaging, in spread-spectrum synthetic-aperture imaging, the Doppler ensemble is used by acquiring frames from multiple firings, each from a unique array element or virtual source that is randomly selected without following a linear right-to-left or left-to-right order, thus causing the slow-time Doppler signal of the off-focus or out-of-cell clutter objects to have random phase, while keeping the phase of in-focus or in-cell objects intact. As a result, the Doppler spectra of the out-of-cell objects is spread throughout the entire frequency spectrum, and is thus suppressed without the need for coherent frame compounding and achieving a Doppler sample rate of PRF as opposed PRF/N as in conventional synthetic aperture imaging. As a result, high spatial resolution and high unaliased Doppler frequencies can be obtained simultaneously.

Embodiments disclosed herein, or portions thereof, can be implemented by programming one or more computer systems or devices with computer-executable instructions embodied in a non-transitory computer-readable medium. When executed by a processor, these instructions operate to cause these computer systems and devices to perform one or more functions particular to embodiments disclosed herein. Programming techniques, computer languages, devices, and computer-readable media necessary to accomplish this are known in the art.

The computer readable medium is a data storage device that can store data, which can thereafter, be read by a computer system. Examples of a computer readable medium include read-only memory, random-access memory, CD-ROMs, magnetic tape, optical data storage devices and the like. The computer readable medium may be geographically localized or may be distributed over a network coupled computer system so that the computer readable code is stored and executed in a distributed fashion.

Computer-implementation of the system or method typically comprises a memory, an interface and a processor. The types and arrangements of memory, interface and processor may be varied according to implementations. For example, the interface may include a software interface that communicates with an end-user computing device through an Internet connection. The interface may also include a physical electronic device configured to receive requests or queries from an end-user.

Any suitable processor type may be used depending on a specific implementation, including for example, a microprocessor, a programmable logic controller or a field programmable logic array. Moreover, any conventional computer architecture may be used for computer-implementation of the system or method including for example a memory, a mass storage device, a processor (CPU), a Read-Only Memory (ROM), and a Random-Access Memory (RAM) generally connected to a system bus of data-processing apparatus. Memory can be implemented as a ROM, RAM, a combination thereof, or simply a general memory unit. Software modules in the form of routines and/or subroutines for carrying out features of the system or method can be stored within memory and then retrieved and processed via a processor to perform a particular task or function. Similarly, one or more method steps may be encoded as a program component, stored as executable instructions within memory and then retrieved and processed via a processor. A user input device, such as a keyboard, mouse, or another pointing device, can be connected to PCI (Peripheral Component Interconnect) bus. If desired, the software may provide an environment that represents programs, files, options, and so forth by means of graphically displayed icons, menus, and dialog boxes on a computer monitor screen.

Computer-implementation of the system or method may accommodate any type of end-user computing device including computing devices communicating over a networked connection. The computing device may display graphical interface elements for performing the various functions of the system or method. For example, the computing device may be a server, desktop, laptop, notebook, tablet, personal digital assistant (PDA), PDA phone or smartphone, and the like. The computing device may be implemented using any appropriate combination of hardware and/or software configured for wired and/or wireless communication. Communication can occur over a network, for example, where remote control of the system is desired.

If a networked connection is desired the system or method may accommodate any type of network. The network may be a single network or a combination of multiple networks. For example, the network may include the internet and/or one or more intranets, landline networks, wireless networks, and/or other appropriate types of communication networks. In another example, the network may comprise a wireless telecommunications network (e.g., cellular phone network) adapted to communicate with other communication networks, such as the Internet. For example, the network may comprise a computer network that makes use of a TCP/IP protocol (including protocols based on TCP/IP protocol, such as HTTP, HTTPS or FTP).

Embodiments described herein are intended for illustrative purposes without any intended loss of generality. Still further variants, modifications and combinations thereof are contemplated and will be recognized by the person of skill in the art. Accordingly, the foregoing detailed description is not intended to limit scope, applicability, or configuration of claimed subject matter.

What is claimed is:

1. A Doppler shift measurement system comprising:
a random generator outputting a control signal encoding a random selection;
an ultrasonic array transducer for emitting a sequence of transmit pulses at a target and for receiving an echo of each transmit pulse reflected from the target, each transmit pulse independently adjusted to an adjustable steering angle corresponding to a unique random selection so that the sequence of transmit pulses is a random sweep;
the sequence of transmit pulses comprises a plurality of subsequences, each of the plurality of subsequences comprising a unique random ordering of a common set of the adjustable steering angles;
a memory for storing echo data;
a processor connected to the memory for using echo data to extract a Doppler parameter; and
a display for providing a visual representation of the Doppler parameter.

2. The system of claim 1, further comprising a clutter filter applied to the echo data, the clutter filter comprising a comb filter applied after the echo data is reordered such that a corresponding sequence of steering angles follow a linear-sequence sweep instead of the random sweep.

3. The system of claim 1, wherein the plurality of subsequences is at least four subsequences.

4. The system of claim 1, further comprising a clutter filter applied to the echo data, after the echo data is reordered such that a corresponding sequence of steering angles follow a linear-sequence sweep instead of the random sweep.

5. The system of claim 1, wherein the processor is configured to extract the Doppler parameter at a maximum slow-time sampling rate equal to the pulse repetition frequency (PRF).

6. A Doppler shift measurement system comprising:
a random generator outputting a control signal encoding a random selection;
an ultrasonic array transducer for emitting a sequence of transmit pulses at a target and for receiving an echo of each transmit pulse reflected from the target, each transmit pulse independently adjusted to an adjustable steering angle corresponding to a unique random selection so that the sequence of transmit pulses is a random sweep;
a memory for storing echo data;
a processor connected to the memory for using echo data to extract a Doppler parameter; and
a display for providing a visual representation of the Doppler parameter;
wherein a conventional two-step process of compounding a plurality of first images to form a second image, and then using a plurality of the second images as a Doppler ensemble to produce a Doppler image, is replaced with a single step that uses the plurality of first images, acquired using the random sequence of steering angles, as the Doppler ensemble to directly produce the Doppler image, each second image of the plurality of the second images having a higher spatial resolution than each first image of the plurality of the first images.

7. The system of claim 6, wherein the sequence of transmit pulses of a length N provides a maximum clutter suppression equal to $\sqrt{N}$.

8. The system of claim 6, further comprising a clutter filter applied to the echo data, the clutter filter comprising a comb filter applied after the echo data is reordered such that a corresponding sequence of steering angles follow a linear-sequence sweep instead of the random sweep.

9. The system of claim 6, further comprising a clutter filter applied to the echo data, after the echo data is reordered such that a corresponding sequence of steering angles follow a linear-sequence sweep instead of the random sweep.

10. The system of claim 6, wherein the processor is configured to extract the Doppler parameter at a maximum slow-time sampling rate equal to the pulse repetition frequency (PRF).

11. A Doppler shift measurement method comprising:
selecting a random steering angle;
transmitting a plurality of ultrasonic transmit pulses directed by a random sequence of adjustable steering angles; the random sequence of adjustable steering angles comprises a plurality of subsequences, each of the plurality of subsequences comprising a unique random ordering of a common set of the adjustable steering angles;
receiving echo data corresponding to each transmit pulse;
storing the echo data in memory;
using the stored echo data to extract a Doppler parameter; and
displaying a visual representation of the Doppler parameter.

12. The method of claim 11, further comprising applying a clutter filter to the echo data, the clutter filter comprising a comb filter applied after the echo data is reordered such that a corresponding sequence of steering angles follow a linear-sequence sweep instead of the random sweep.

13. The method of claim 11, wherein the plurality of subsequences is at least four subsequences.

14. The method of claim 11, further comprising reordering the echo data such that a corresponding sequence of steering angles follow a linear-sequence sweep instead of a random sweep and further comprising filtering the reordered echo data.

15. The method of claim 11, wherein a maximum slow-time sampling rate for extracting the Doppler parameter is equal to the pulse repetition frequency (PRF).

16. A Doppler shift measurement method comprising:
selecting a random steering angle;
transmitting a plurality of ultrasonic transmit pulses directed by a random sequence of adjustable steering angles;
receiving echo data corresponding to each transmit pulse;
storing the echo data in memory;
using the stored echo data to extract a Doppler parameter; and
displaying a visual representation of the Doppler parameter;
producing a Doppler flow image that does not comprise a two-step process of compounding a plurality of first images to form a second image, and then using a plurality of the second images as a Doppler ensemble to produce the Doppler flow image, but instead comprises a one-step process that uses the plurality of first images, acquired using the random sequence of transmit steering angles, as the Doppler ensemble to directly produce the high resolution Doppler flow image, each second image of the plurality of the second images having a higher spatial resolution than each first image of the plurality of the first images.

17. The method of claim 16, wherein the sequence of transmit pulses of a length N provides a maximum clutter suppression equal to $\sqrt{N}$.

18. The method of claim 16, further comprising applying a clutter filter to the echo data, the clutter filter comprising a comb filter applied after the echo data is reordered such that a corresponding sequence of steering angles follow a linear-sequence sweep instead of the random sweep.

19. The method of claim 16, further comprising reordering the echo data such that a corresponding sequence of steering angles follow a linear-sequence sweep instead of a random sweep and further comprising filtering the reordered echo data.

20. The method of claim 16, wherein a maximum slow-time sampling rate for extracting the Doppler parameter is equal to the pulse repetition frequency (PRF).

* * * * *